(12) United States Patent
Yamauchi

(10) Patent No.: US 12,279,752 B2
(45) Date of Patent: Apr. 22, 2025

(54) INSPECTION ANALYSIS METHOD AND INSPECTION ANALYSIS SYSTEM

(71) Applicant: Evident Corporation, Nagano (JP)

(72) Inventor: Hideyoshi Yamauchi, Akiruno (JP)

(73) Assignee: Evident Corporation, Nagano (JP)

( * ) Notice: Subject to any disclaimer, the term of this patent is extended or adjusted under 35 U.S.C. 154(b) by 412 days.

(21) Appl. No.: 17/857,455

(22) Filed: Jul. 5, 2022

(65) Prior Publication Data

US 2023/0009448 A1  Jan. 12, 2023

(30) Foreign Application Priority Data

Jul. 12, 2021 (JP) .................... 2021-115136

(51) Int. Cl.
| | |
|---|---|
| *A61B 1/005* | (2006.01) |
| *A61B 1/00* | (2006.01) |
| *A61B 1/045* | (2006.01) |
| *A61B 1/06* | (2006.01) |
| *G06V 10/10* | (2022.01) |

(52) U.S. Cl.
CPC ........ *A61B 1/0051* (2013.01); *A61B 1/00045* (2013.01); *A61B 1/045* (2013.01); *A61B 1/0676* (2013.01); *G06V 10/17* (2022.01)

(58) Field of Classification Search
USPC ...................................................... 382/128
See application file for complete search history.

(56) References Cited

U.S. PATENT DOCUMENTS

2020/0074655 A1* 3/2020 Sakamoto ............... G06T 7/579
2022/0385874 A1* 12/2022 Sakamoto ............ H04N 13/156
2023/0030432 A1* 2/2023 Shigehisa ................ A61B 5/06

FOREIGN PATENT DOCUMENTS

JP         2014-209196 A    11/2014

* cited by examiner

*Primary Examiner* — Jacky X Zheng
(74) *Attorney, Agent, or Firm* — Scully, Scott, Murphy & Presser, P.C.

(57) ABSTRACT

An inspection analysis method includes an analysis step, a prediction step, and an output step. A processor analyzes inspection information related to an operation in an inspection and generates first operation data and second operation data indicating a content of the operation in the analysis step. The first operation data indicate a content of the operation in a first inspection. The second operation data indicate a content of the operation in a second inspection performed after the first inspection is completed. The processor compares the first operation data and the second operation data with each other and predicts a state of an inspection target in the prediction step. The processor outputs state information indicating the state to a reporting device in the output step.

16 Claims, 19 Drawing Sheets

FIG. 19

| | PAST AVERAGE VALUE | CURRENT VALUE |
|---|---|---|
| BENDING-TIMES NUMBER | 50 | 100 |
| STILL-IMAGE-ACQUISITION-TIMES NUMBER | 10 | 20 |
| MEASUREMENT-EXECUTION-TIMES NUMBER | 10 | 5 |
| INSERTION TIME | 120 | 60 |
| ... | ... | ... |

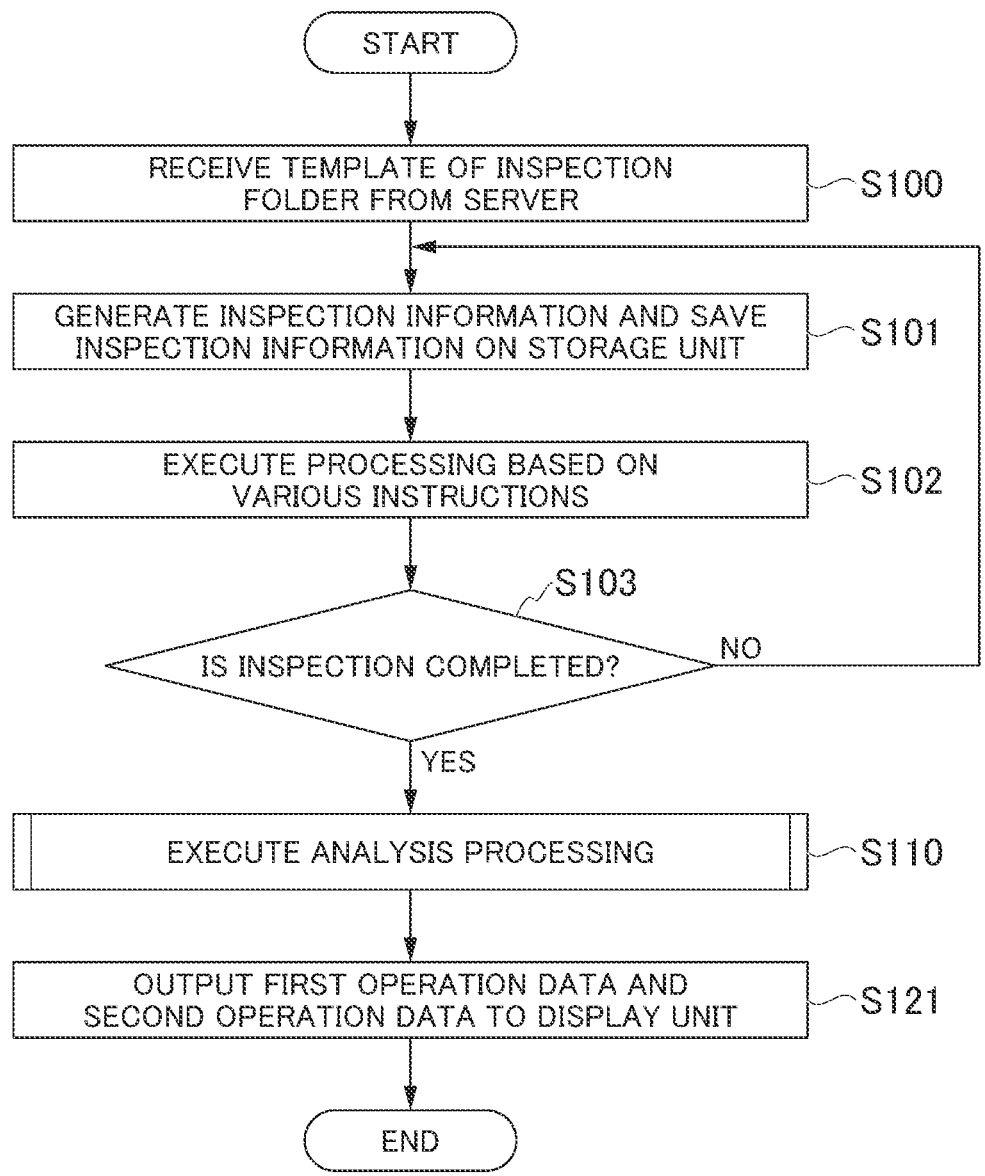

INSPECTION ANALYSIS METHOD AND INSPECTION ANALYSIS SYSTEM

BACKGROUND OF THE INVENTION

Field of the Invention

The present invention relates to an inspection analysis method and an inspection analysis system.

Priority is claimed on Japanese Patent Application No. 2021-115136, filed on Jul. 12, 2021, the content of which is incorporated herein by reference.

Description of Related Art

Industrial endoscope devices have been used for inspection of internal damage, corrosion, and the like of boilers, pipes, aircraft engines, and the like. In the fields of industrial endoscope devices, a service using a server on a network (cloud) is provided. In such a service, an endoscope device transmits an image acquired in an inspection to a server. The server saves the image received from the endoscope device. The server analyzes an inspection result on the basis of the image and executes failure prediction or the like.

A technique disclosed in Japanese Unexamined Patent Application, First Publication No. 2014-209196 provides an inspection system using a cloud. The inspection system includes an inspection device and a mobile device. Data acquired by the inspection device are transmitted to the mobile device via the cloud. The mobile device analyzes an inspection result and generates a report. The report is shared via the cloud.

SUMMARY OF THE INVENTION

According to a first aspect of the present invention, an inspection analysis method analyzes an operation performed by a user in an inspection performed by inserting an endoscope into an inspection target. The inspection analysis method includes an analysis step, a prediction step, and an output step. A processor analyzes inspection information related to the operation and generates first operation data and second operation data indicating a content of the operation in the analysis step. The operation includes a first operation of the endoscope and a second operation related to an image generated by an imaging device disposed in a distal end of the endoscope. The first operation data indicate a content of the operation in a first inspection. The second operation data indicate a content of the operation in a second inspection performed after the first inspection is completed. The processor compares the first operation data and the second operation data with each other and predicts a state of the inspection target in the prediction step. The processor outputs state information indicating the state to a reporting device in the output step.

According to a second aspect of the present invention, in the first aspect, an inspection analysis method analyzes an operation performed by a user in an inspection performed by inserting an endoscope into an inspection target. The inspection analysis method includes an analysis step and an output step. A processor analyzes inspection information related to the operation and generates first operation data and second operation data indicating a content of the operation in the analysis step. The operation includes a first operation of the endoscope and a second operation related to an image generated by an imaging device disposed in a distal end of the endoscope. The first operation data indicate a content of the operation in a first inspection. The second operation data indicate a content of the operation in a second inspection performed after the first inspection is completed. The processor outputs the first operation data and the second operation data to a reporting device in the output step.

According to a third aspect of the present invention, in the first aspect, the processor may calculate, in the analysis step, an insertion amount indicating a length of a portion of the endoscope inserted in the inspection target when the user performs the operation. The processor may compare the first operation data and the second operation data with each other on the basis of the insertion amount in the prediction step.

According to a fourth aspect of the present invention, in the second aspect, the processor may calculate, in the analysis step, an insertion amount indicating a length of a portion of the endoscope inserted in the inspection target when the user performs the operation. The processor may associate the first operation data and the second operation data with each other on the basis of the insertion amount in the analysis step.

According to a fifth aspect of the present invention, in the third aspect, the processor may determine a start timing of the inspection and a completion timing of the inspection on the basis of the insertion amount in the analysis step. The processor may analyze the inspection information generated from the start timing of the first inspection to the completion timing of the first inspection and generates the first operation data in the analysis step. The processor may analyze the inspection information generated from the start timing of the second inspection to the completion timing of the second inspection and generates the second operation data in the analysis step.

According to a sixth aspect of the present invention, in the fourth aspect, the processor may determine a start timing of the inspection and a completion timing of the inspection on the basis of the insertion amount in the analysis step. The processor may analyze the inspection information generated from the start timing of the first inspection to the completion timing of the first inspection and generates the first operation data in the analysis step. The processor may analyze the inspection information generated from the start timing of the second inspection to the completion timing of the second inspection and generates the second operation data in the analysis step.

According to a seventh aspect of the present invention, in the first aspect, the first operation data and the second operation data may include at least one of a bending-times number of the endoscope, a bending amount of the endoscope, and an insertion amount. The bending-times number indicates the number of times the endoscope bends. The bending amount indicates an amount of a change in an angle of the distal end when the endoscope bends. The insertion amount indicates a length of a portion of the endoscope inserted in the inspection target when the user performs the operation.

According to an eighth aspect of the present invention, in the second aspect, the first operation data and the second operation data may include at least one of a bending-times number of the endoscope, a bending amount of the endoscope, an insertion amount, and an insertion time. The bending-times number indicates the number of times the endoscope bends. The bending amount indicates an amount of a change in an angle of the distal end when the endoscope bends. The insertion amount indicates a length of a portion of the endoscope inserted in the inspection target when the user performs the operation. The insertion time indicates a length of time during which the endoscope is inserted in the inspection target.

According to a ninth aspect of the present invention, in the third aspect, the endoscope may be capable of being housed in a state of being wound around a reel. The insertion amount may indicate a length of a portion of the endoscope pulled out of the reel.

According to a tenth aspect of the present invention, in the fourth aspect, the endoscope may be capable of being housed in a state of being wound around a reel. The insertion amount may indicate a length of a portion of the endoscope pulled out of the reel.

According to an eleventh aspect of the present invention, in the seventh aspect, the endoscope may be capable of being housed in a state of being wound around a reel. The insertion amount may indicate a length of a portion of the endoscope pulled out of the reel.

According to a twelfth aspect of the present invention, in the eighth aspect, the endoscope may be capable of being housed in a state of being wound around a reel. The insertion amount may indicate a length of a portion of the endoscope pulled out of the reel.

According to a thirteenth aspect of the present invention, in the first aspect, the first operation data and the second operation data may include at least one of the number of times a still image is acquired, the number of times measurement using the image is executed, and a result of the measurement.

According to a fourteenth aspect of the present invention, in the second aspect, the first operation data and the second operation data may include at least one of the number of times a still image is acquired, the number of times measurement using the image is executed, a length of time required for acquiring the still image, a length of time required for executing the measurement, and the number of times a parameter of image processing using the image is set.

According to a fifteenth aspect of the present invention, in the first aspect, a type of the inspection target in the second inspection may be the same as that of the inspection target in the first inspection. An individual of the inspection target in the second inspection may be the same as or different from that of the inspection target in the first inspection.

According to a sixteenth aspect of the present invention, in the second aspect, a type of the inspection target in the second inspection may be the same as that of the inspection target in the first inspection. An individual of the inspection target in the second inspection may be the same as or different from that of the inspection target in the first inspection.

According to a seventeenth aspect of the present invention, in the first aspect, after the second inspection is completed, the processor may output the state information to the reporting device in the output step.

According to an eighteenth aspect of the present invention, in the second aspect, after the second inspection is completed, the processor may output the first operation data and the second operation data to the reporting device in the output step.

According to a nineteenth aspect of the present invention, an inspection analysis method analyzes an operation performed by a user in an inspection performed by inserting an endoscope into an inspection target. The inspection analysis method includes an analysis step and an output step. A processor analyzes inspection information related to the operation and generates operation data indicating a content of the operation in the analysis step. The operation includes a first operation of the endoscope and a second operation related to an image generated by an imaging device disposed in a distal end of the endoscope. The processor outputs the operation information to a reporting device in the output step.

According to a twentieth aspect of the present invention, an inspection analysis system analyzes an operation performed by a user in an inspection performed by inserting an endoscope into an inspection target. The inspection analysis system includes an inspection analysis device and an endoscope device. The inspection analysis device includes a first processor and a first communicator. The first processor is configured to analyze inspection information related to the operation. The operation includes a first operation of the endoscope and a second operation related to an image generated by an imaging device disposed in a distal end of the endoscope. The first processor is configured to generate first operation data and second operation data indicating a content of the operation. The first operation data indicate a content of the operation in a first inspection. The second operation data indicate a content of the operation in a second inspection performed after the first inspection is completed. The first processor is configured to compare the first operation data and the second operation data with each other. The first processor is configured to predict a state of the inspection target. The first communicator is configured to receive the inspection information from the endoscope device and transmit state information indicating the state to the endoscope device. The endoscope device includes the endoscope, a second communicator, and a second processor. The second communicator is configured to transmit the inspection information to the inspection analysis device and receive the state information from the inspection analysis device. The second processor is configured to output the state information to a reporting device.

According to a twenty-first aspect of the present invention, an inspection analysis system analyzes an operation performed by a user in an inspection performed by inserting an endoscope into an inspection target. The inspection analysis system includes an inspection analysis device and an endoscope device. The inspection analysis device includes a first processor and a first communicator. The first processor is configured to analyze inspection information related to the operation. The operation includes a first operation of the endoscope and a second operation related to an image generated by an imaging device disposed in a distal end of the endoscope. The first processor is configured to generate first operation data and second operation data indicating a content of the operation. The first operation data indicate a content of the operation in a first inspection. The second operation data indicate a content of the operation in a second inspection performed after the first inspection is completed. The first communicator is configured to receive the inspection information from the endoscope device and transmit the first operation data and the second operation data to the endoscope device. The endoscope device includes the endoscope, a second communicator, and a second processor. The second communicator is configured to transmit the inspection information to the inspection analysis device and receive the first operation data and the second operation data from the inspection analysis device. The second processor is configured to output the first operation data and the second operation data to a reporting device.

BRIEF DESCRIPTION OF THE DRAWINGS

FIG. 19 is a diagram showing an example of a report in the second embodiment of the present invention.

FIG. 21 is a flow chart showing a procedure of processing executed by the endoscope device according to the modified example of the second embodiment of the present invention.

DETAILED DESCRIPTION OF THE INVENTION

Hereinafter, embodiments of the present invention will be described with reference to the drawings. An inspection target in each embodiment of the present invention is an industrial product. The inspection target includes one or more inspection portions. For example, in a case in which the inspection target is an aircraft engine, the inspection portion is a combustion tube, a high pressure turbine, or the like.

First Embodiment

Figure 1:
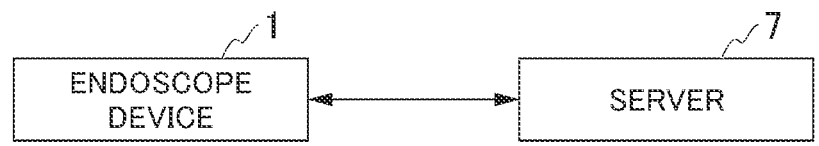
FIG. 1 is a block diagram showing a configuration of an inspection analysis system according to a first embodiment of the present invention.

A first embodiment of the present invention will be described. FIG. 1 shows a configuration of an inspection analysis system 10 according to the first embodiment. The inspection analysis system 10 provides a service that executes failure prediction of an inspection target and that notifies a user of prediction of the inspection target. The inspection analysis system 10 shown in FIG. 1 includes an endoscope device 1 and a server 7. The endoscope device 1 and the server 7 communicate with each other. For example, the server 7 is a cloud server.

Figure 2:
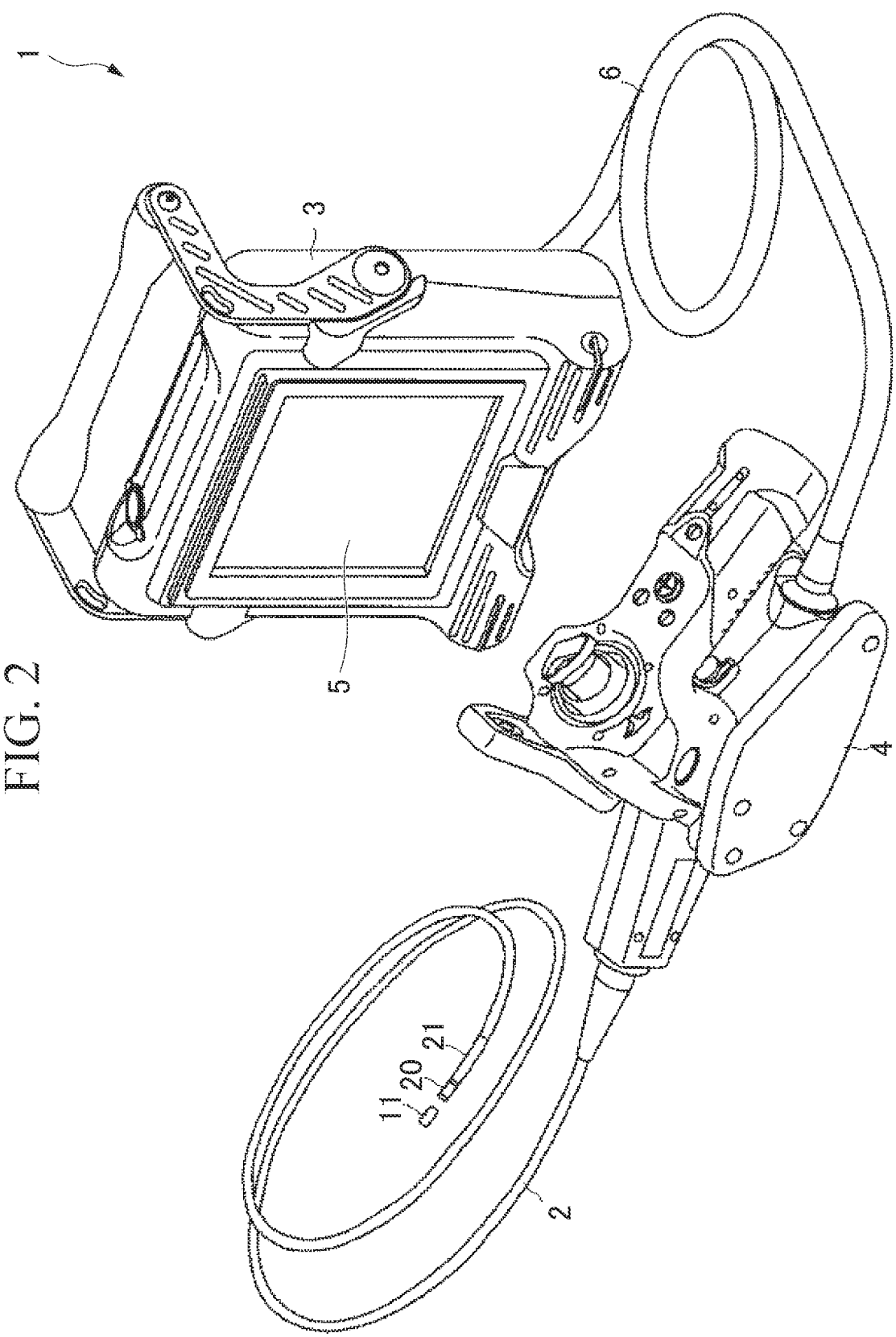
FIG. 2 is a perspective view showing an entire configuration of an endoscope device according to the first embodiment of the present invention.

FIG. 2 shows an external appearance of the endoscope device 1. The endoscope device 1 shown in FIG. 2 includes an insertion unit 2, a main body unit 3, an operation unit 4, a display unit 5, and a cable 6.

The insertion unit 2 constitutes an endoscope. The insertion unit 2 is inserted into the inside of an inspection target. A distal end portion 20 is disposed at the distal end of the insertion unit 2. The insertion unit 2 has a long and thin bendable tube shape from the distal end portion 20 to a base end portion. An optical adapter 11 is mounted on the distal end portion 20. A bending portion 21 is disposed on the base end side of the distal end portion 20. The bending portion 21 is capable of bending in a predetermined direction. The base end portion of the insertion unit 2 is connected to the operation unit 4.

The operation unit 4 includes a button, a joystick, and the like for a user to perform an operation. The operation unit 4 is connected to the main body unit 3 by the cable 6. The user inputs a bending instruction, a still image acquisition instruction, a measurement instruction, or the like into the endoscope device 1 by operating the operation unit 4. The bending instruction indicates an instruction to bend the bending portion 21. The still image acquisition instruction indicates an instruction to acquire a still image. The measurement instruction indicates an instruction to execute measurement using a still image. The operation unit 4 outputs the instruction input by the user to the main body unit 3.

The display unit 5 is disposed on the surface of the main body unit 3. The display unit 5 is a monitor (display) such as a liquid crystal display (LCD). The display unit 5 may be a touch panel wirelessly connected to the main body unit 3. In a case in which the display unit 5 is configured as the touch panel, a user touches the display screen of the display unit 5 by using a part of the body or a tool. For example, the part of the body is a finger.

Figure 3:
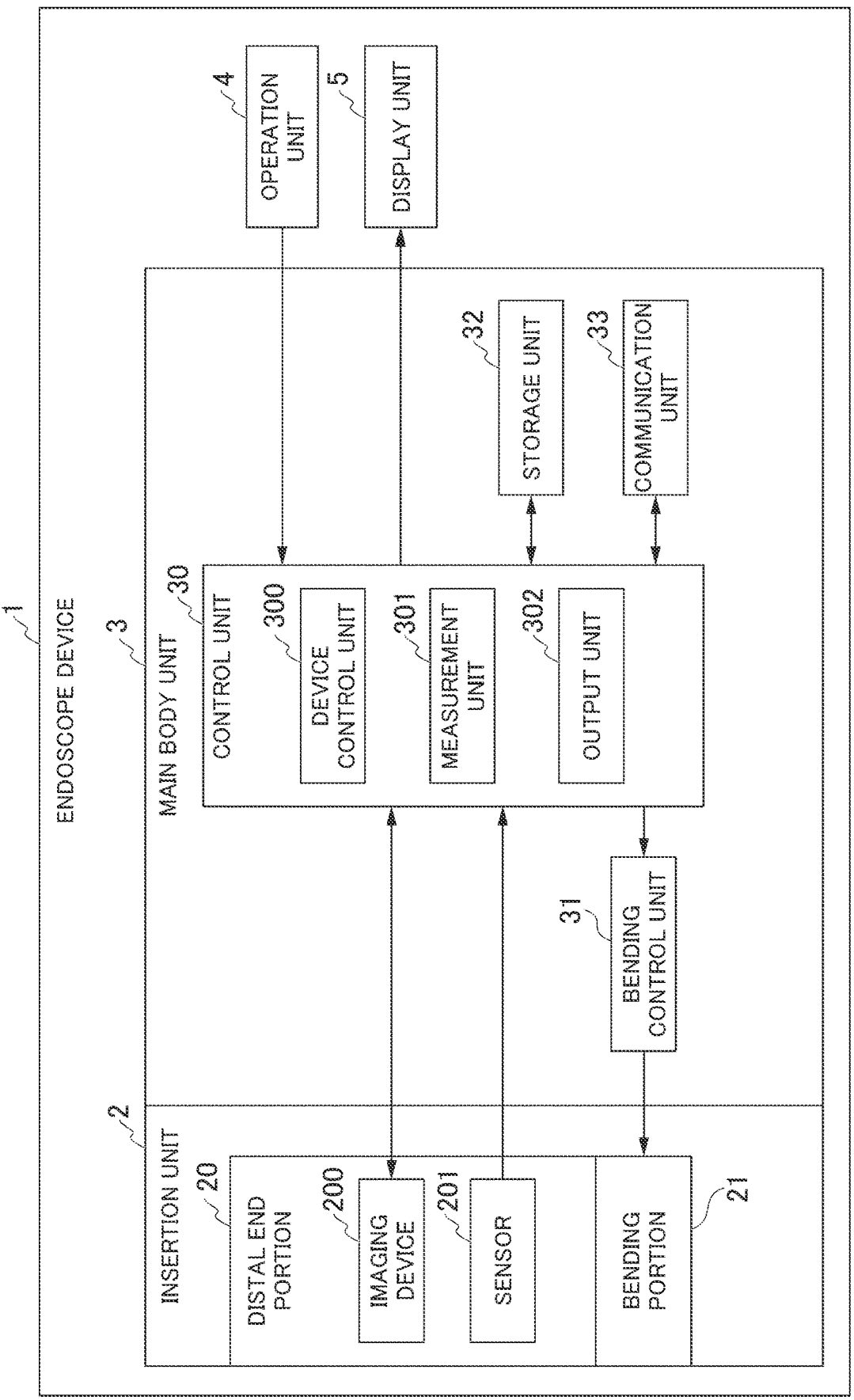
FIG. 3 is a block diagram showing a configuration of the endoscope device according to the first embodiment of the present invention.

FIG. 3 shows a configuration of the endoscope device 1. The distal end portion shown in FIG. 3 includes an imaging device 200 and a sensor 201. The imaging device 200 is an image sensor such as a CCD sensor or a CMOS sensor. The imaging device 200 sequentially generates two or more images (frames). The two or more images constitute a video. The imaging device 200 outputs each generated image to the main body unit 3. When the still image acquisition instruction is output from the main body unit 3, the imaging device 200 generates one or more still images and outputs the generated still images to the main body unit 3.

The sensor 201 is an acceleration sensor or a gyro sensor (angular velocity sensor). The acceleration sensor determines an acceleration of the distal end portion 20. The gyro sensor determines an angular velocity of the distal end portion 20. The sensor 201 may be a combination of the acceleration sensor and the gyro sensor. The sensor 201 may be a six-axis inertial sensor that determines accelerations of three axes and angular velocities of three axes.

The sensor 201 measures a physical quantity and outputs sensor information indicating the physical quantity. The physical quantity is an acceleration or an angular velocity. The sensor information indicates the acceleration of the distal end portion 20 or the angular velocity of the distal end portion 20.

The main body unit 3 shown in FIG. 3 includes a control unit 30, a bending control unit 31, a storage unit 32, and a communication unit 33. The control unit 30 includes a device control unit 300, a measurement unit 301, and an output unit 302.

The device control unit 300 controls the entire endoscope device 1. In addition, the device control unit 300 generates inspection information related to an operation performed by a user in an inspection.

The device control unit 300 accepts the instruction output from the operation unit 4. When the bending instruction is output from the operation unit 4, the device control unit 300 outputs the bending instruction to the bending control unit 31. When the still image acquisition instruction is output from the operation unit 4, the device control unit 300 outputs the still image acquisition instruction to the imaging device 200.

The device control unit 300 acquires the sensor information output from the sensor 201. The device control unit 300 generates inspection information including the bending instruction, the still image acquisition instruction, the measurement instruction, the sensor information, and time point information. The time point information indicates a time point at which the device control unit 300 accepts the bending instruction, the still image acquisition instruction, or the measurement instruction. In addition, the time point information indicates a time point at which the device control unit 300 acquires the sensor information. The device control unit 300 stores the inspection information on the storage unit 32. For example, the inspection information is configured as text data.

When the measurement instruction is output from the operation unit 4, the measurement unit 301 executes the measurement by using a still image generated by the imaging device 200. For example, the measurement unit 301 calculates a three-dimensional distance (3D distance) between two points on a subject in an inspection target in a first measurement mode. The measurement unit 301 calculates the area of a three-dimensional region determined by three or more points on the subject in a second measurement mode. The measurement unit 301 calculates a 3D distance between a point on the subject and a three-dimensional straight line determined by two points on the subject in a third measurement mode. The measurement unit 301 calculates a 3D distance between a point on the subject and a three-dimensional region determined by three points on the subject in a fourth measurement mode.

A user may designate the type of the measurement when inputting the measurement instruction. The type of the measurement indicates any one of the first to fourth measurement modes. The type of the measurement is not limited to the above-described examples.

The output unit 302 outputs state information indicating the state of an inspection target to the display unit 5, thus displaying the state information on the display unit 5. The state information is received from the server 7 by the communication unit 33.

The control unit 30 is constituted by at least one of a processor and a logic circuit. For example, the processor is at least one of a central processing unit (CPU), a digital signal processor (DSP), and a graphics-processing unit (GPU). For example, the logic circuit is at least one of an application-specific integrated circuit (ASIC) and a field-programmable gate array (FPGA). The control unit 30 may include one or a plurality of processors. The control unit 30 may include one or a plurality of logic circuits.

A computer of the endoscope device 1 may read a program and execute the read program. The program includes commands defining the operations of the control unit 30. In other words, the functions of the control unit 30 may be realized by software.

The program described above, for example, may be provided by using a "computer-readable storage medium" such as a flash memory. The program may be transmitted from the computer storing the program to the endoscope device 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

The bending control unit 31 bends the bending portion 21 on the basis of the bending instruction.

The storage unit 32 is a volatile or nonvolatile recording medium. For example, the storage unit 32 is at least one of a random-access memory (RAM), a dynamic random-access memory (DRAM), a static random-access memory (SRAM), a read-only memory (ROM), an erasable programmable read-only memory (EPROM), an electrically erasable programmable read-only memory (EEPROM), and a flash memory. The storage unit 32 stores the inspection information. The storage unit 32 may store a video and a still image generated by the imaging device 200.

The communication unit 33 is a communicator including a communication circuit. The communication unit 33 performs communication with the server 7. The communication unit 33 transmits the inspection information stored on the storage unit 32 to the server 7. The communication unit 33 receives the state information transmitted from the server 7.

In general, an inspection is performed as follows. An inspection target includes an access port for inserting the insertion unit 2 into the inspection target. A user inserts the insertion unit 2 into the inspection target through the access port. When the distal end portion 20 of the insertion unit 2 comes close to an inspection portion, the user inputs the bending instruction into the endoscope device 1 and bends the bending portion 21. In this way, the user adjusts the composition of photographing.

Thereafter, the user inputs the still image acquisition instruction into the endoscope device 1 and causes the endoscope device 1 to acquire a still image. In a case in which the measurement needs to be executed, the user inputs the measurement instruction into the endoscope device 1 and causes the endoscope device 1 to execute the measurement.

The operation performed by the user includes a first operation of the insertion unit 2 and a second operation related to an image generated by the imaging device 200. The first operation corresponds to both an operation performed by the user to input the bending instruction into the endoscope device 1 and an operation performed by the user to insert the insertion unit 2 into an inspection target. The second operation corresponds to both an operation performed by the user to input the still image acquisition instruction into the endoscope device 1 and an operation performed by the user to input the measurement instruction into the endoscope device 1.

The state information includes at least one of damage detection information, damage change information, and oversight information. The damage detection information indicates damage that was not detected in a past inspection excluding the latest inspection and was detected in the latest inspection. In other words, the damage detection information indicates newly detected damage. The damage change information indicates a change in a state of damage detected in a past inspection. For example, the damage change information indicates that the area of the damage has increased or the damage has progressed in the depth direction. The oversight information indicates that an oversight of an inspection portion or an oversight of damage has occurred. The damage is a concave, a convex, a crack, or the like.

Figure 4:
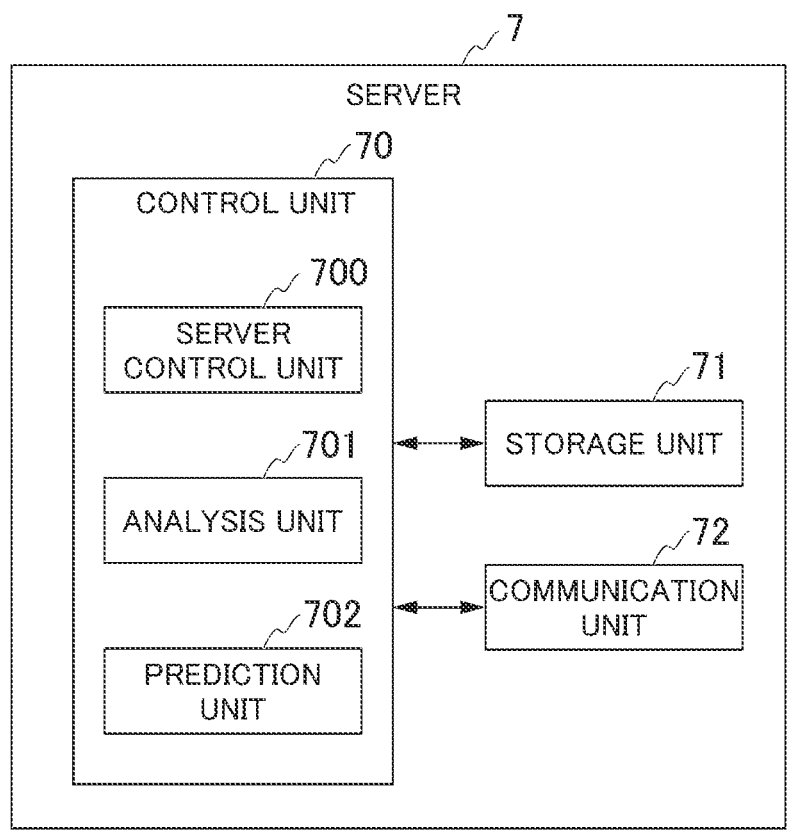
FIG. 4 is a block diagram showing a configuration of a server according to the first embodiment of the present invention.

FIG. 4 shows a configuration of the server 7. The server 7 shown in FIG. 4 includes a control unit 70, a storage unit 71, and a communication unit 72. The control unit 70 includes a server control unit 700, an analysis unit 701, and a prediction unit 702.

The server control unit 700 controls the entire server 7. The analysis unit 701 analyzes the inspection information and generates operation data. The operation data indicate a content of an operation performed by a user in an inspection.

The operation data include at least one of a bending-times number, a bending amount, and an insertion amount. The bending-times number, the bending amount, and the insertion amount indicate a content of the first operation related to the insertion unit 2. The bending-times number indicates the number of times the bending portion 21 bends. The bending amount indicates the amount of a change in the angle of the distal end portion 20 when the bending portion 21 bends. The insertion amount indicates the length of a portion of the insertion unit 2 inserted in an inspection target when a user performs an operation.

In addition, the operation data include at least one of a still-image-acquisition-times number, a measurement-execution-times number, and a measurement result. The still-image-acquisition-times number, the measurement-execution-times number, and the measurement result indicate a content of the second operation related to an image. The still-image-acquisition-times number indicates the number of times the imaging device 200 generates a still image. The still-image-acquisition-times number is the same as the number of still images. The measurement-execution-times number indicates the number of times the measurement unit 301 executes measurement using a still image. The measurement result indicates the 3D distance or the area calculated by the measurement unit 301.

The analysis unit 701 analyzes the inspection information of a past inspection (first inspection) and generates first operation data. In addition, the analysis unit 701 analyzes the inspection information of the latest inspection (second inspection) and generates second operation data. The second inspection is an inspection performed last. The first inspection is an inspection performed once or more before the second inspection is performed.

The prediction unit 702 compares the first operation data and the second operation data with each other and predicts a state of an inspection target. The prediction unit 702 generates state information indicating the state of the inspection target.

The control unit 70 is constituted by at least one of a processor and a logic circuit. The control unit 70 may include one or a plurality of processors. The control unit 70 may include one or a plurality of logic circuits.

A computer of the server 7 may read a program and execute the read program. The program includes commands defining the operations of the control unit 70. In other words, the functions of the control unit 70 may be realized by software. The program may be realized similarly to that realizing the functions of the control unit 30.

The storage unit 71 is a nonvolatile recording medium. For example, the storage unit 71 is at least one of an SRAM, an EPROM, an EEPROM, and a flash memory. The storage unit 71 stores the inspection information.

The communication unit 72 is a communicator including a communication circuit. The communication unit 72 performs communication with the endoscope device 1. The communication unit 72 receives the inspection information transmitted from the endoscope device 1. The inspection information received by the communication unit 72 is saved on the storage unit 71. The communication unit 72 transmits the state information generated by the prediction unit 702 to the endoscope device 1.

Figure 5:
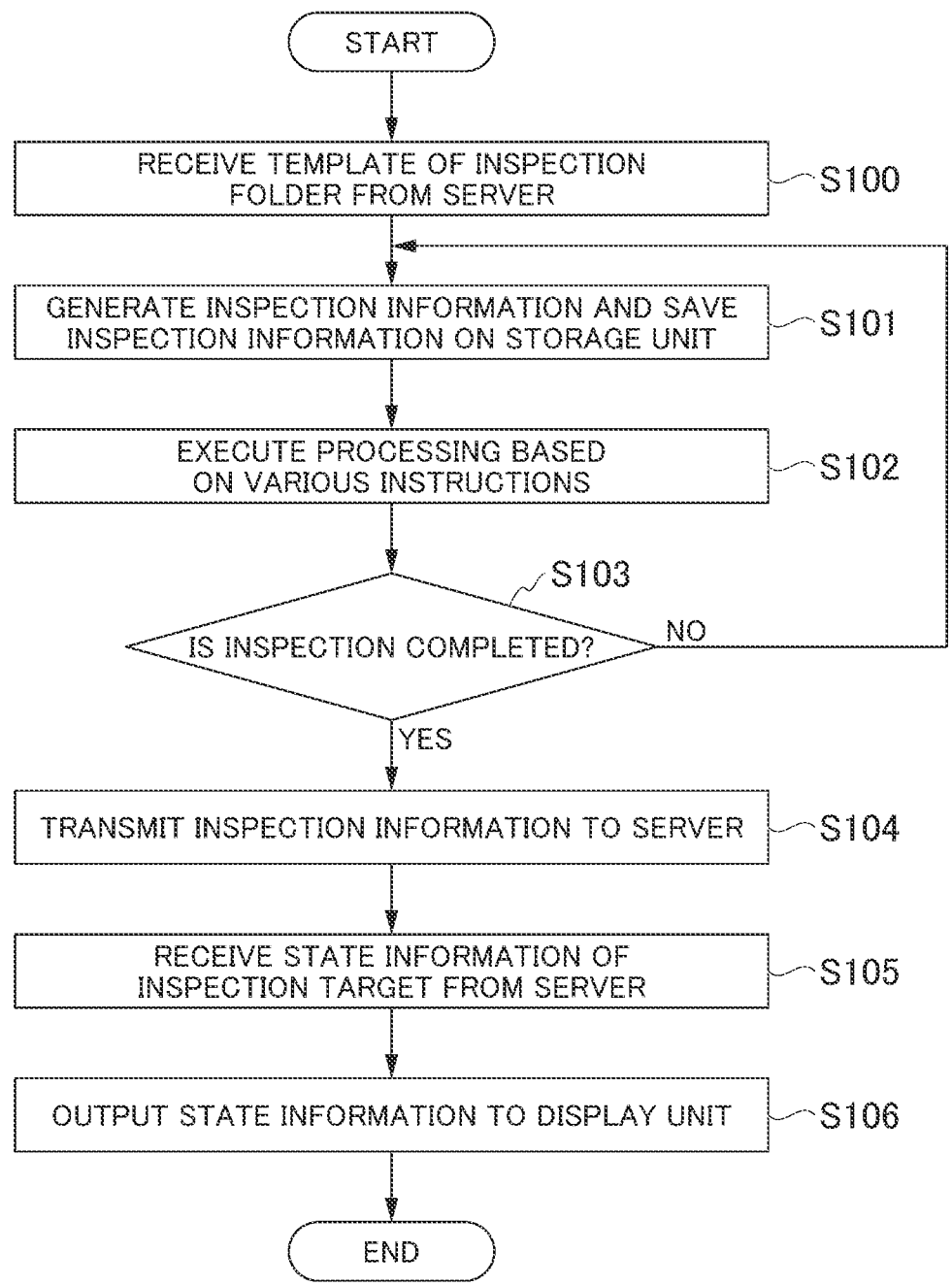
FIG. 5 is a flow chart showing a procedure of processing executed by the endoscope device according to the first embodiment of the present invention.

Processing executed by the endoscope device 1 will be described by using FIG. 5. FIG. 5 shows a procedure of the processing executed by the endoscope device 1.

The communication unit 33 receives a template of an inspection folder from the server 7 (Step S100). The received template is stored on the storage unit 32.

Data of a still image or the like are acquired in an inspection. The data are saved in a folder in the storage unit 32. A template of a folder is prepared for each inspection target in the storage unit 71 of the server 7. The communication unit 33 receives the template in Step S100. The template includes two or more folders. Each of the folders is prepared for each inspection portion. The name of each of the folders is the same as that of the inspection portion.

A user inputs a selection instruction to select an inspection portion into the endoscope device 1 by operating the operation unit 4. The device control unit 300 selects one folder corresponding to the inspection portion indicated by the selection instruction. After the folder is selected, the following processing is executed.

After Step S100, the device control unit 300 generates inspection information including a bending instruction, a still image acquisition instruction, sensor information, measurement information, and time point information, and saves the inspection information on the storage unit 32 (Step S101). The bending instruction, the still image acquisition instruction, the sensor information, the measurement information, and the time point information are associated with each other. The measurement information includes a measurement instruction and a measurement result. The inspection information is saved in the folder selected on the basis of the selection instruction.

In a case in which the device control unit 300 has not received the bending instruction or the still image acquisition instruction at a timing at which Step S101 is executed, the inspection information does not need to include the bending instruction or does not need to include the still image acquisition instruction. In addition, in a case in which the device control unit 300 has not received the measurement instruction at a timing at which Step S101 is executed, the inspection information does not need to include the measurement information.

After Step S101, the device control unit 300 executes processing on the basis of the bending instruction, the still image acquisition instruction, or the measurement instruction. When the bending instruction is output from the operation unit 4, the device control unit 300 outputs the bending instruction to the bending control unit 31. The bending control unit 31 bends the bending portion 21 on the basis of the bending instruction. When the still image acquisition instruction is output from the operation unit 4, the device control unit 300 outputs the still image acquisition instruction to the imaging device 200. The imaging device 200 generates one or more still images on the basis of the still image acquisition instruction. When the measurement instruction is output from the operation unit 4, the device control unit 300 causes the measurement unit 301 to execute the measurement (Step S102). In a case in which the device control unit 300 has not received one of the bending instruction, the still image acquisition instruction, and the measurement instruction at a timing at which Step S101 is executed, processing related to the one of the bending instruction, the still image acquisition instruction, and the measurement instruction does not need to be executed.

After Step S102, the device control unit 300 determines whether the inspection is completed (Step S103). For example, a user inputs an instruction indicating completion of the inspection into the endoscope device 1 by operating the operation unit 4. In a case in which the device control unit 300 accepts the instruction, the device control unit 300 determines that the inspection is completed. In a case in which the device control unit 300 does not accept the instruction, the device control unit 300 determines that the inspection is not completed.

When the device control unit 300 determines that the inspection is not completed in Step S103, Step S101 is executed. When the device control unit 300 determines that the inspection is completed in Step S103, the device control unit 300 outputs the inspection information stored on the storage unit 32 to the communication unit 33. The device control unit 300 transmits the inspection information to the server 7 by controlling the communication unit 33 (Step S104).

After Step S104, the device control unit 300 receives state information from the server 7 by controlling the communication unit 33 (Step S105).

After Step S105, the output unit 302 outputs the state information received in Step S105 to the display unit 5 (Step S106). The display unit 5 displays the state information. For example, when the inspection is completed or a new inspection is started, Step S106 is executed. When Step S106 is executed, the processing shown in FIG. 5 is completed.

After the inspection in one inspection portion is completed, a user may input a selection instruction to select another inspection portion into the endoscope device 1 by operating the operation unit 4. The device control unit 300 selects one folder corresponding to the inspection portion indicated by the selection instruction. After the folder is selected, the processing in Steps S101 to S103 may be executed.

Figure 6:
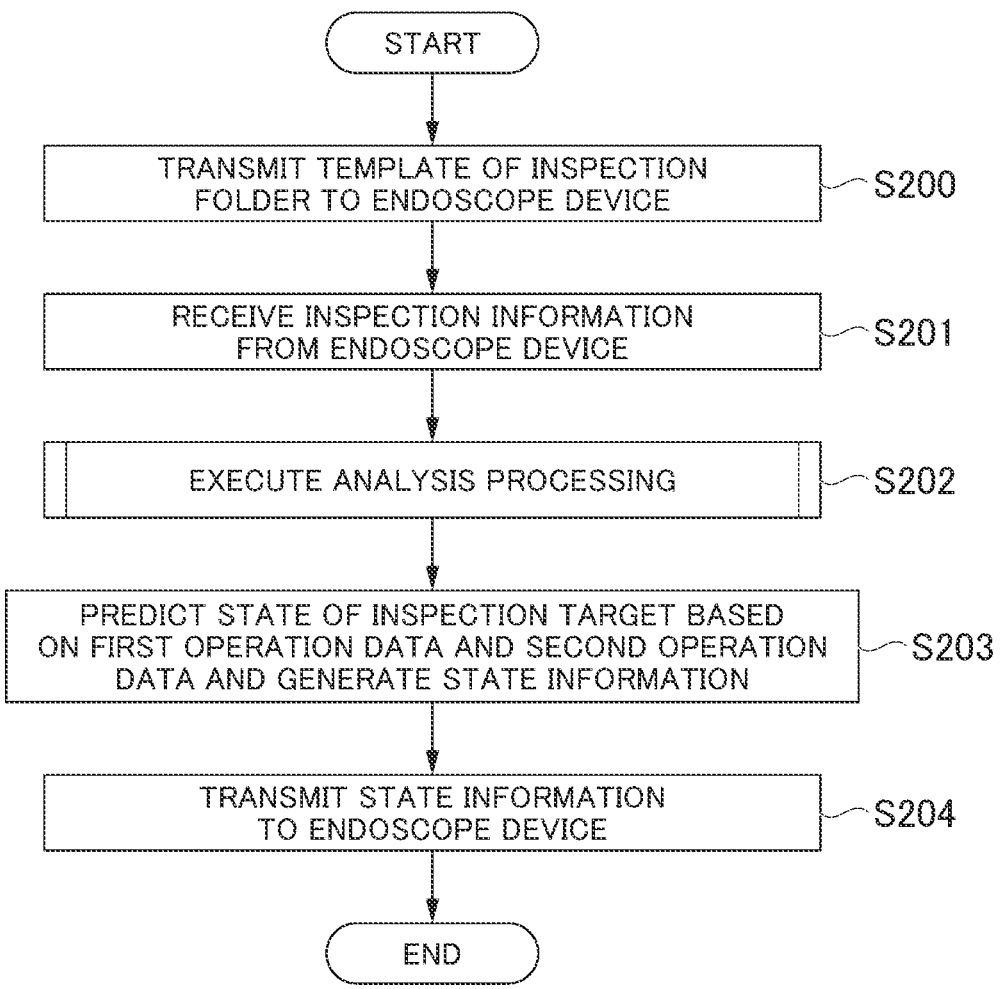
FIG. 6 is a flow chart showing a procedure of processing executed by the server according to the first embodiment of the present invention.

Processing executed by the server 7 will be described by using FIG. 6. FIG. 6 shows a procedure of the processing executed by the server 7.

The server control unit 700 transmits a template of an inspection folder to the endoscope device 1 by controlling the communication unit 72 (Step S200).

After Step S200, the server control unit 700 receives inspection information from the endoscope device 1 by controlling the communication unit 72 (Step S201). The inspection information received from the endoscope device 1 is saved on the storage unit 71.

After Step S201, the analysis unit 701 executes analysis processing by using the inspection information stored on the storage unit 71 (Step S202).

Figure 7:
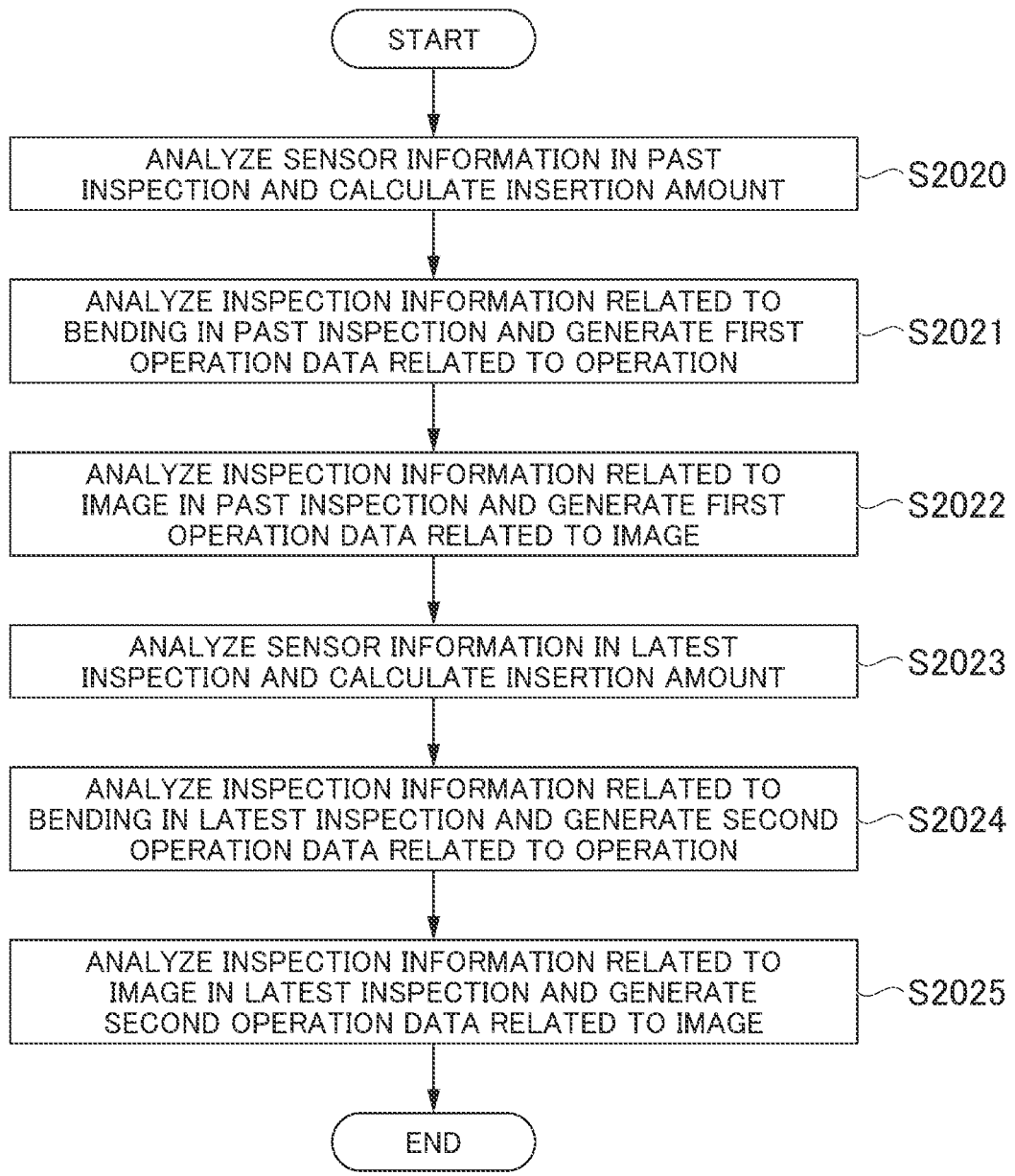
FIG. 7 is a flow chart showing a procedure of analysis processing in the first embodiment of the present invention.

The analysis processing executed in Step S202 will be described by using FIG. 7. FIG. 7 shows a procedure of the analysis processing.

The analysis unit 701 analyzes the sensor information in a past inspection and calculates an insertion amount (Step S2020).

The analysis unit 701 executes the following processing in Step S2020. The analysis unit 701 analyzes the sensor information in the past inspection. The sensor information indicates an acceleration. The analysis unit 701 calculates a position of the distal end portion 20 at each time point by using the acceleration. The analysis unit 701 calculates an insertion amount at each time point by using the calculated position.

For example, the analysis unit 701 calculates an insertion amount on the basis of a change in the position of the distal end portion 20 from a start time point of an inspection to a completion time point of the inspection. For example, a user inputs an instruction indicating start of the inspection into the endoscope device 1 by operating the operation unit 4. The start time point of the inspection indicates a time point at which the device control unit 300 accepts the instruction. The completion time point of the inspection indicates a time point at which the device control unit 300 accepts an instruction indicating completion of the inspection.

An endoscope device including a long insertion unit may be used. The insertion unit may be housed in a main body unit with the insertion unit being wound around a reel in the main body unit. When the insertion unit is inserted in an inspection target, the insertion unit is pulled out of the reel. The device control unit 300 may generate inspection information including information indicating the amount of rotation of the reel. The analysis unit 701 may calculate an insertion amount on the basis of the amount of rotation of the reel. The insertion amount may indicate the length of a portion of the insertion unit pulled out of the reel by rotation of the reel. The entire portion is not necessarily inserted into the inspection target. The portion may include a first portion inserted in the inspection target and a second portion not inserted in the inspection target.

After Step S2020, the analysis unit 701 generates operation data related to bending by using the inspection information related to bending in the past inspection. The analysis unit 701 generates first operation data including the insertion amount and the operation data related to bending (Step S2021). The first operation data relate to an operation performed by a user in the past inspection.

The analysis unit 701 executes the following processing in Step S2021. The inspection information related to bending includes a bending instruction, sensor information, and time point information. The sensor information indicates at least one of an acceleration and an angular velocity. The analysis unit 701 calculates a bending amount and a bending-times number.

The analysis unit 701 calculates a bending amount (bending angle) of the bending portion 21 by using the acceleration or the angular velocity. The bending portion 21 may bend in an angle in accordance with the length of time during which a user tilts a joystick of the operation unit 4. In such a case, the analysis unit 701 may calculate the bending amount of the bending portion 21 by calculating the length of time during which the bending instruction is output from the operation unit 4. The bending portion 21 may bend in an angle in accordance with the angle of the joystick when a user tilts the joystick. In such a case, the analysis unit 701 may calculate the bending amount of the bending portion 21 on the basis of the angle of the joystick indicated by the bending instruction.

The analysis unit 701 calculates a bending-times number on the basis of the bending amount of the bending portion 21. For example, the analysis unit 701 compares the bending amount with a predetermined amount and calculates the bending-times number.

Figure 8:
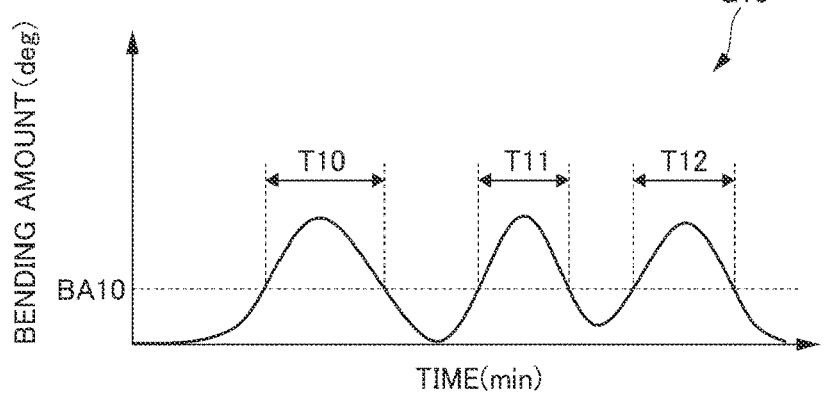
FIG. 8 is a graph showing an example of a change in a bending amount in the first embodiment of the present invention.

A graph G10 shown in FIG. 8 shows an example of a change in the bending amount. The horizontal axis in the graph G10 indicates time, and the vertical axis in the graph G10 indicates the bending amount. The analysis unit 701 compares the bending amount at each time point with a predetermined amount BA10. After the bending amount becomes greater than the predetermined amount BA10, the bending amount becomes less than the predetermined amount BA10. If a change in the bending amount like this is detected, the analysis unit 701 detects bending once. In the example shown in FIG. 8, the bending amount is greater than or equal to the predetermined amount BA10 in each of a period T10, a period T11, and a period T12. Therefore, the bending-times number in the example shown in FIG. 8 is three.

The bending amount and the bending-times number correspond to the operation data related to bending. The analysis unit 701 generates first operation data including the bending amount, the bending-times number, and the insertion amount. The bending amount, the bending-times number, and the insertion amount are associated with each other.

The analysis unit 701 may calculate a bending-times number of the bending portion 21 in a specific direction. The analysis unit 701 may calculate a sum of the bending-times numbers of the bending portion 21 in two or more directions.

After Step S2021, the analysis unit 701 generates operation data related to an image by using the inspection information related to an image in the past inspection. The analysis unit 701 associates the operation data related to an image with the insertion amount, thus generating first operation data related to the image (Step S2022).

The analysis unit 701 executes the following processing in Step S2022. The inspection information related to an image includes a still image acquisition instruction, measurement information, and time point information. The analysis unit 701 calculates the number of times the still image acquisition instruction is output from the operation unit 4, thus calculating a still-image-acquisition-times number. The still-image-acquisition-times number may be an average or a median of still-image-acquisition-times numbers in two or more past inspections.

In addition, the analysis unit 701 calculates a measurement-execution-times number by using the measurement information. For example, the analysis unit 701 calculates the number of times a measurement mode is selected, thus calculating the measurement-execution-times number. The analysis unit 701 may calculate the measurement-execution-times number by calculating the number of measurement results. The measurement-execution-times number may be an average or a median of measurement-execution-times numbers in two or more past inspections. There is a case in which the measurement unit 301 executes a multiple types of measurement. The analysis unit 701 may calculate the measurement-execution-times number for each type of measurement.

The analysis unit 701 may calculate all of the still-image-acquisition-times number, the measurement-execution-times number, and the measurement result. The analysis unit 701 may calculate only some of the still-image-acquisition-times number, the measurement-execution-times number, and the measurement result.

After Step S2022, the analysis unit 701 analyzes the sensor information in the latest inspection and calculates an insertion amount (Step S2023). The analysis unit 701 executes, in Step S2023, similar processing to Step S2020.

After Step S2023, the analysis unit 701 generates operation data related to bending by using the inspection information related to bending in the latest inspection. The analysis unit 701 generates second operation data including the insertion amount and the operation data related to bending (Step S2024). The second operation data relate to an operation performed by a user in the latest inspection. The analysis unit 701 executes, in Step S2024, similar processing to Step S2021.

After Step S2024, the analysis unit 701 generates operation data related to an image by using the inspection information related to an image in the latest inspection. The analysis unit 701 associates the operation data related to an image with the insertion amount, thus generating second operation data related to the image (Step S2025). The analysis unit 701 executes, in Step S2025, similar processing to Step S2022. When Step S2025 is executed, the analysis processing is completed.

The procedure of an inspection is determined in advance. In a case in which the state of an inspection target does not change, the content of an operation is expected not to change between different inspections. However, there is a case in which the state of the inspection target changes and the content of an operation changes between different inspections. The analysis unit 701 detects a change in the state of the inspection target by analyzing the inspection information.

The analysis unit 701 analyzes the inspection information and detects an operation performed by a user. The analysis unit 701 can determine a position in the inspection target on the basis of the insertion amount. The analysis unit 701 can determine a position at which the user performs the operation by associating the detected operation and the insertion amount with each other.

The order of processing executed in the analysis processing is not limited to that shown in FIG. 7. The six steps shown in FIG. 7 may be executed in arbitrary order.

The analysis unit 701 may determine a start timing of an inspection and a completion timing of the inspection on the basis of the insertion amount. For example, when the insertion amount increases from zero, the analysis unit 701 may determine that the inspection is started. When the insertion amount decreases and reaches zero, the analysis unit 701 may determine that the inspection is completed. In a case in which a predetermined insertion amount corresponding to the position of the access port is known, the analysis unit 701 may user the predetermined insertion amount. For example, when the insertion amount increases from the predetermined insertion amount, the analysis unit 701 may determine that the inspection is started. When the insertion amount decreases and reaches the predetermined insertion amount, the analysis unit 701 may determine that the inspection is completed.

The analysis unit 701 may analyze the inspection information generated from the start timing of the past inspection to the completion timing of the past inspection and may generate the first operation data. The analysis unit 701 may analyze the inspection information generated from the start timing of the latest inspection to the completion timing of the latest inspection and may generate the second operation data.

Processing executed by the server 7 will be described by using FIG. 6 again. After Step S202, the prediction unit 702 compares the first operation data and the second operation data with each other and predicts a state of an inspection target. The prediction unit 702 generates state information indicating the state of the inspection target (Step S203).

Figure 9:
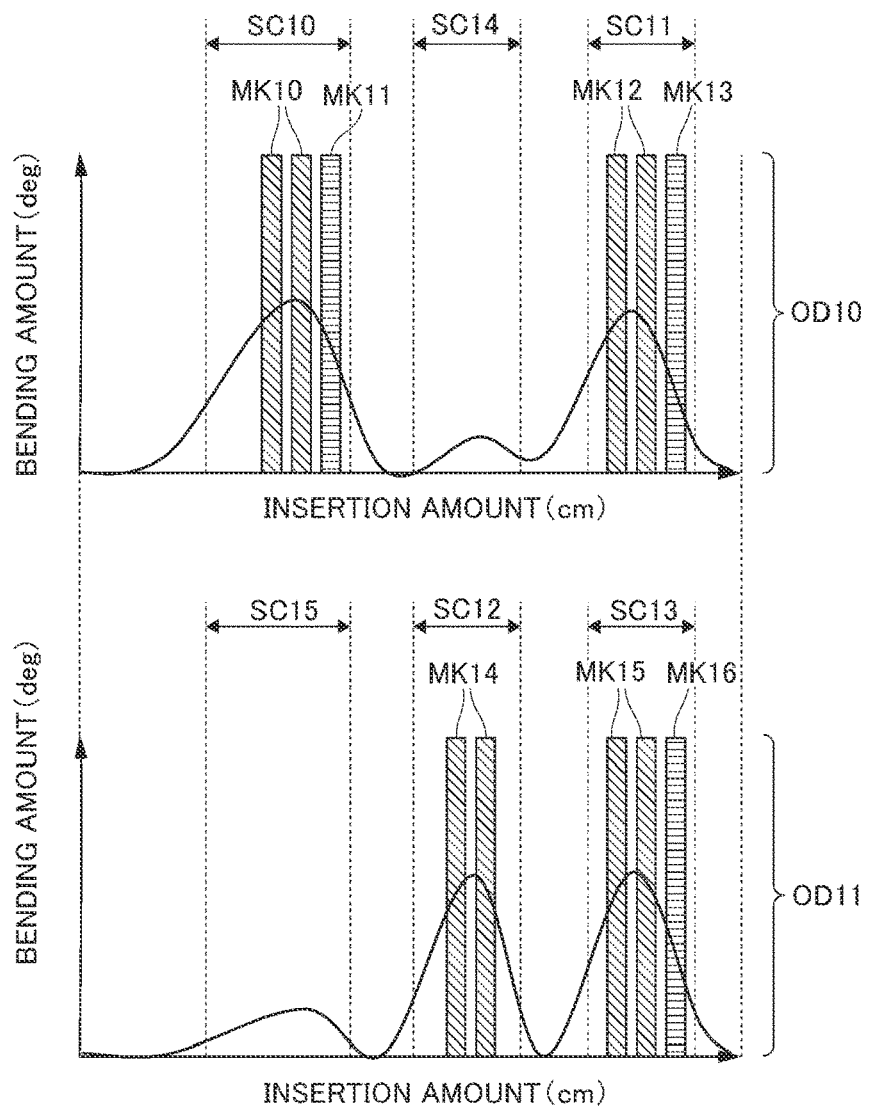
FIG. 9 is a diagram showing an example of operation data in the first embodiment of the present invention.

The processing executed by the prediction unit 702 in Step S203 will be described by using FIG. 9. FIG. 9 shows an example of the operation data.

First operation data OD10 indicate operation data in a past inspection. Second operation data OD11 indicate operation data in the latest inspection. The first operation data OD10 and the second operation data OD11 indicate a bending amount, a still-image-acquisition-times number, a measurement-execution-times number, and an insertion amount.

The relationship between the bending amount and the insertion amount is shown as a graph. The horizontal axis in the graph indicates the insertion amount, and the vertical axis in the graph indicates the bending amount. The insertion amount corresponds to a position in an inspection target.

The length of time required for an inspection is different between inspections. Therefore, the bending amount or the like is associated with the insertion amount, not time. The analysis unit 701 associates the first operation data and the second operation data with each other on the basis of the insertion amount. The prediction unit 702 compares the first operation data and the second operation data with each other on the basis of the insertion amount.

The bending amount is relatively large in a section SC10 and a section SC11 of the graph shown by the first operation data OD10. Marks MK10 and a mark MK11 are shown in the section SC10. Marks MK12 and a mark MK13 are shown in the section SC11.

The marks MK10 and the marks MK12 indicate positions at which a still image was acquired in the past inspection. The mark MK11 and the mark MK13 indicate positions at which the measurement was executed in the past inspection. In the section SC10, a still image was acquired twice as the marks MK10 show, and the measurement was executed once as the mark MK11 shows. In the section SC11, a still image was acquired twice as the marks MK12 show, and the measurement was executed once as the mark MK13 shows.

The bending amount is relatively large in a section SC12 and a section SC13 of the graph shown by the second operation data OD11. Marks MK14 are shown in the section SC12. Marks MK15 and a mark MK16 are shown in the section SC13.

The marks MK14 and the marks MK15 indicate positions at which a still image was acquired in the latest inspection. The mark MK16 indicates positions at which the measurement was executed in the latest inspection. In the section SC12, a still image was acquired twice as the marks MK14 show. In the section SC13, a still image was acquired twice as the marks MK15 show, and the measurement was executed once as the mark MK16 shows.

The side surface of the inspection target or complex structures are inspected in many cases. Therefore, it is highly probable that an inspection portion was inspected in a section in which the bending amount is large. Proof of an inspection at the position at which the inspection is performed needs to be recorded. Therefore, it is highly probable that the inspection portion was inspected in a section in which a still image was acquired or the measurement was executed.

The prediction unit 702 determines whether damage was newly detected on the basis of the still-image-acquisition-times number or the measurement-execution-times number. When the latest inspection was performed, a still image was acquired in the section SC12. When the past inspection was performed, a still image was not acquired in a section SC14 corresponding to the section SC12. This indicates a possibility that damage newly occurred in a period from the timing at which the past inspection was performed to the timing at which the latest inspection was performed. Therefore, the prediction unit 702 determines that damage was newly detected. The prediction unit 702 generates damage detection information associated with the insertion amount in the section SC12. The insertion amount corresponds to the position of the damage.

The prediction unit 702 may determine whether damage was newly detected on the basis of the bending amount. The bending amount was relatively large in the section SC12 when the latest inspection was performed. When the past inspection was performed, the bending amount was relatively small in the section SC14 corresponding to the section SC12. Therefore, the prediction unit 702 may determine that damage was newly detected.

The prediction unit 702 may determine whether damage was newly detected on the basis of the bending-times number. When the bending amount is greater than or equal to a predetermined amount, the prediction unit 702 determines that the bending portion 21 bends once. When the latest inspection was performed, the bending portion 21 bended once in the section SC12. When the past inspection was performed, the bending portion 21 did not bend in the section SC14 corresponding to the section SC12. Therefore, the prediction unit 702 may determine that damage was newly detected.

There is a case in which only observation of an inspection portion is performed without acquiring a still image of the inspection portion or measuring the inspection portion. The prediction unit 702 can determine that a user observed damage by using the bending amount.

The prediction unit 702 may generate damage detection information of damage commonly detected in the past inspection and the latest inspection. When the past inspection was performed, a still image was acquired and the measurement was executed in the section SC11. When the latest inspection was performed, a still image was acquired and the measurement was executed in the section SC13. The insertion amount in at least part of the section SC13 is the same as that in the section SC11. The prediction unit 702 may determine that damage was commonly detected in the past inspection and the latest inspection.

The prediction unit 702 determines whether damage changed on the basis of the measurement result. When the past inspection was performed, the measurement was executed in the section SC11. When the latest inspection was performed, the measurement was executed in the section SC13. The prediction unit 702 compares the measurement result (first measurement result) in the section SC11 and the measurement result (second measurement result) in the section SC13 with each other. When the second measurement result is greater than the first measurement result, the prediction unit 702 determines that the damage grew large. The prediction unit 702 generates damage change information associated with the insertion amount in the section SC13. The insertion amount corresponds to the position of the damage.

The prediction unit 702 determines whether an oversight of an inspection portion or an oversight of damage occurred on the basis of the still-image-acquisition-times number or the measurement-execution-times number. When the past inspection was performed, a still image was acquired and the measurement was executed in the section SC10. When the latest inspection was performed, a still image was not acquired and the measurement was not executed in a section SC15 corresponding to the section SC10. Therefore, the prediction unit 702 determines that an oversight of an inspection portion or an oversight of damage occurred. The prediction unit 702 generates oversight information associated with the insertion amount in the section SC15. The insertion amount corresponds to the position at which the oversight occurred.

The prediction unit 702 may determine whether an oversight of an inspection portion or an oversight of damage occurred on the basis of the bending amount. When the past inspection was performed, the bending amount was relatively large in the section SC10. When the latest inspection was performed, the bending amount was small in the section SC15 corresponding to the section SC10. Therefore, the prediction unit 702 may determine that an oversight of an inspection portion or an oversight of damage occurred.

The prediction unit 702 may determine whether an oversight of an inspection portion or an oversight of damage occurred on the basis of the bending-times number. When the past inspection was performed, the bending portion 21 bended once in the section SC10. When the latest inspection was performed, the bending portion 21 did not bend in the section SC15 corresponding to the section SC10. Therefore, the prediction unit 702 may determine that an oversight of an inspection portion or an oversight of damage occurred.

The prediction unit 702 generates state information including the damage detection information, the damage change information, and the oversight information. The prediction unit 702 may generate state information including only some of the damage detection information, the damage change information, and the oversight information.

Figure 10:
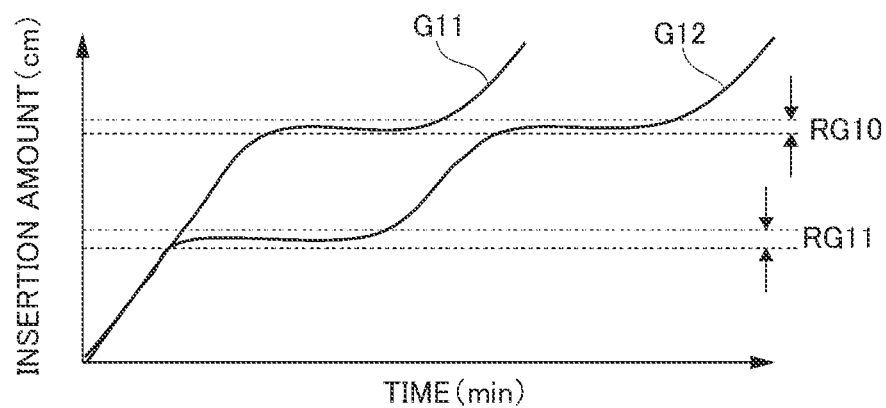
FIG. 10 is a graph showing an example of a change in an insertion amount in the first embodiment of the present invention.

The prediction unit 702 may determine whether damage was newly detected on the basis of the insertion amount. For example, the prediction unit 702 may compare a temporal change in the insertion amount in the past inspection and a temporal change in the insertion amount in the latest inspection with each other. A graph G11 and a graph G12 shown in FIG. 10 show an example of a change in the insertion amount. The horizontal axis in each graph indicates time, and the vertical axis in each graph indicates the insertion amount.

The graph G11 shows a temporal change in the insertion amount in the past inspection. The graph G12 shows a temporal change in the insertion amount in the latest inspection. In a range RG10 shown in FIG. 10, the temporal change shown by each of the graph G11 and the graph G12 is small. In addition, in a range RG11 shown in FIG. 10, the temporal change shown by the graph G12 is small. When a temporal change in the insertion amount is small, the distal end portion 20 of the insertion unit 2 is stationary. In this case, there is a possibility that a still image is acquired or the measurement is executed. The prediction unit 702 can determine that damage was detected in a position corresponding to each of the range RG10 and the range RG11.

The range RG10 is detected in both the graph G11 and the graph G12. On the other hand, the range RG11 is not detected in the graph G11 and is detected only in the graph G12. In other words, when the latest inspection was performed, there is a possibility that damage was newly detected in the range RG11 in which damage was not detected in the past inspection. Therefore, the prediction unit 702 may determine that damage was newly detected.

Figure 11:
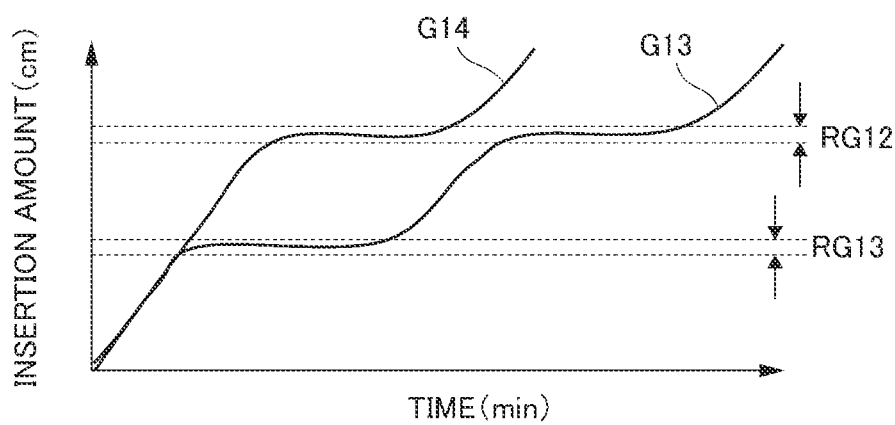
FIG. 11 is a graph showing an example of a change in an insertion amount in the first embodiment of the present invention.

The prediction unit 702 may determine whether an oversight of an inspection portion or an oversight of damage occurred on the basis of the insertion amount. For example, the prediction unit 702 may compare a temporal change in the insertion amount in the past inspection and a temporal change in the insertion amount in the latest inspection with each other. A graph G13 and a graph G14 shown in FIG. 11 show an example of a change in the insertion amount. The horizontal axis in each graph indicates time, and the vertical axis in each graph indicates the insertion amount.

The graph G13 shows a temporal change in the insertion amount in the past inspection. The graph G14 shows a temporal change in the insertion amount in the latest inspection. In a range RG12 shown in FIG. 11, the temporal change shown by each of the graph G13 and the graph G14 is small. In addition, in a range RG13 shown in FIG. 11, the temporal change shown by the graph G13 is small. The prediction unit 702 can determine that damage was detected in a position corresponding to each of the range RG12 and the range RG13.

The range RG12 is detected in both the graph G13 and the graph G14. On the other hand, the range RG13 is not detected in the graph G14 and is detected only in the graph G13. In other words, when the latest inspection was performed, there is a possibility that damage was looked over in the range RG13 in which the damage was detected in the past inspection. Therefore, the prediction unit 702 may determine that an oversight of an inspection portion or an oversight of the damage occurred.

After the insertion unit 2 is inserted to the deepest portion of an inspection target, there is a case in which a user performs an inspection while pulling out the insertion unit 2. In this case, the prediction unit 702 may generate the state information by using a similar method to that shown in FIG. 9, FIG. 10, or FIG. 11.

The prediction unit 702 may generate the state information by using any two or more of the still-image-acquisition-times number, the measurement-execution-times number, the bending amount, the bending-times number, and the insertion amount.

Processing executed by the server 7 will be described by using FIG. 6 again. After Step S203, the server control unit 700 transmits the state information generated in Step S203 to the endoscope device 1 by controlling the communication unit 72 (Step S204). When Step S204 is executed, the processing shown in FIG. 6 is completed.

Figure 12:
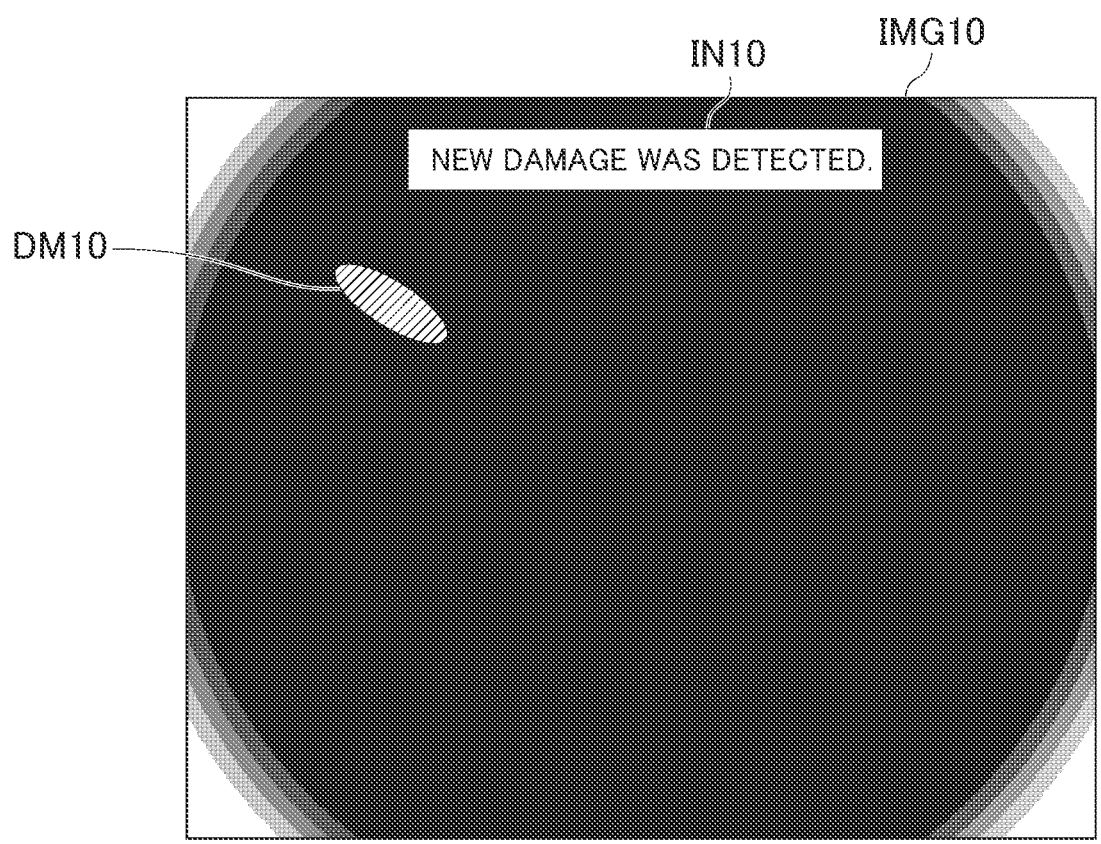
FIG. 12 is a diagram showing an example of an image displayed on a display unit included in the endoscope device according to the first embodiment of the present invention.

FIG. 12 shows an example of an image displayed on the display unit 5 in Step S106 shown in FIG. 5. After a new inspection is started, the display unit 5 displays an image IMG10. The image IMG10 constitutes a video.

When the insertion amount of the insertion unit 2 matches the insertion amount indicated by the damage detection information, the output unit 302 outputs information corresponding to the damage detection information to the display unit 5. The display unit 5 displays information IN10. The information IN10 indicates that new damage was detected. For example, damage DM10 is seen in the image IMG10. The damage DM10 is damage detected in the latest inspection.

When the insertion amount of the insertion unit 2 matches the insertion amount indicated by the damage change information, the output unit 302 may output information corresponding to the damage change information to the display unit 5. For example, the information indicates that damage grew large.

When the insertion amount of the insertion unit 2 matches the insertion amount indicated by the oversight information, the output unit 302 may output information corresponding to the oversight information to the display unit 5. For example, the information indicates that damage was overlooked in the latest inspection.

The output unit 302 outputs the state information to the display unit 5, and the display unit 5 displays the state information. A method of outputting the state information is not limited to this. The output unit 302 may output the state information to a reporting device other than the display unit 5.

The output unit 302 may output sound data to a speaker and may cause the speaker to generate a sound corresponding to the state information. The speaker may generate a message sound corresponding to the state information. Alternatively, the speaker may generate a sound having a pattern corresponding to the state information.

The output unit 302 may output a control signal indicating a pattern of vibration to a vibration generator and may cause the vibration generator to generate vibration having the pattern corresponding to the state information. The output unit 302 may output a control signal indicating a pattern of light emission to a light source and may cause the light source to generate light having the pattern corresponding to the state information.

A model number is given to an inspection target in accordance with the type of the inspection target. In addition, a serial number is given to an individual of the inspection target. When the model number of an inspection target A is the same as that of an inspection target B, the inspection target A and the inspection target B are inspection targets of the same type. When the model number of an inspection target A is the same as that of an inspection target B and the serial number of the inspection target A is different from that of the inspection target B, the inspection target A and the inspection target B are inspection targets of the same type and are different individuals.

For example, the analysis unit 701 analyzes the inspection information in a past inspection for an inspection target A1 and analyzes the inspection information in the latest inspection for the inspection target A1. There is a case in which the inspection information in the latest inspection for the inspection target A1 exists and the inspection information in the past inspection for the inspection target A1 does not exist. In such a case, the analysis unit 701 analyzes the inspection information in the past inspection for an inspection target A2 and analyzes the inspection information in the latest inspection for the inspection target A1. The model number of the inspection target A1 is the same as that of the inspection target A2. The serial number of the inspection target A1 is different from that of the inspection target A2. In other words, the inspection target A1 and the inspection target A2 are inspection targets of the same type and are different individuals.

An inspection analysis method according to each aspect of the present invention provides a method of analyzing an operation performed by a user in an inspection performed by inserting the insertion unit 2 (endoscope) into an inspection target. The operation includes a first operation of the insertion unit 2 and a second operation related to an image generated by the imaging device 200 disposed in the distal end portion 20 of the insertion unit 2. The inspection analysis method includes an analysis step, a prediction step, and an output step. The analysis unit 701 analyzes inspection information related to the operation and generates first operation data and second operation data indicating a content of the operation in the analysis step (Step S202). The first operation data indicate a content of an operation in a first inspection. The second operation data indicate a content of an operation in a second inspection performed after the first inspection is completed. The prediction unit 702 compares the first operation data and the second operation data with each other and predicts a state of the inspection target in the prediction step (Step S203). The output unit 302 outputs state information indicating the state of the inspection target to the display unit 5 (reporting device) in the output step (Step S106).

An inspection analysis system according to each aspect of the present invention includes the server 7 (inspection analysis device) and the endoscope device 1. The server 7 includes the analysis unit 701, the prediction unit 702, and the communication unit 72 (first communication unit). The analysis unit 701 analyzes inspection information related to an operation performed by a user and generates first operation data and second operation data indicating a content of the operation. The prediction unit 702 compares the first operation data and the second operation data with each other and predicts a state of the inspection target. The communication unit 72 receives the inspection information from the endoscope device 1 and transmits state information indicating the state of the inspection target to the endoscope device 1. The endoscope device 1 includes the insertion unit 2 (endoscope), the communication unit 33 (second communication unit), and the output unit 302. The communication unit 33 transmits the inspection information to the server 7 and receives the state information from the server 7. The output unit 302 outputs the state information to the display unit 5 (reporting device).

Each aspect of the present invention may include the following modified example. The analysis unit 701 calculates, in the analysis step (Step S202), an insertion amount indicating the length of a portion of the insertion unit 2 (endoscope) inserted in the inspection target when the user performs an operation. The prediction unit 702 compares the first operation data and the second operation data with each other on the basis of the insertion amount in the prediction step (Step S203).

Each aspect of the present invention may include the following modified example. The analysis unit 701 determines a start timing of an inspection and a completion timing of the inspection on the basis of the insertion amount in the analysis step (Step S202). The analysis unit 701 analyzes the inspection information generated from the start timing of a first inspection to the completion timing of the first inspection and generates the first operation data in the analysis step. The analysis unit 701 analyzes the inspection information generated from the start timing of a second inspection to the completion timing of the second inspection and generates the second operation data in the analysis step.

Each aspect of the present invention may include the following modified example. The first operation data and the second operation data include at least one of a bending-times number of the endoscope, a bending amount of the endoscope, and an insertion amount. The insertion amount indicates the length of a portion of the insertion unit 2 (endoscope) inserted in the inspection target when the user performs an operation.

Each aspect of the present invention may include the following modified example. The endoscope is capable of being housed in a state of being wound around a reel. The insertion amount indicates the length of a portion of the endoscope pulled out of the reel.

Each aspect of the present invention may include the following modified example. The first operation data and the second operation data include at least one of the number of times a still image is acquired, the number of times measurement using an image is executed, and a result of the measurement.

Each aspect of the present invention may include the following modified example. The type of an inspection target in the second inspection is the same as that of an inspection target in the first inspection. The individual of the inspection target in the second inspection is the same as or different from that of the inspection target in the first inspection.

Each aspect of the present invention may include the following modified example. After the second inspection is completed, the output unit 302 outputs the state information to the display unit 5 (reporting device) in the output step (Step S106).

In the first embodiment, the analysis unit 701 analyzes the inspection information and generates operation data. The prediction unit 702 predicts a state of an inspection target on the basis of the operation data. Therefore, the inspection analysis system 10 can analyze an inspection result without requiring an image. A user can check a state of the inspection target.

The amount of data of the inspection information is less than that of data of an image. Therefore, the amount of charges in a service using a server on a network is restricted. The inspection information needs to be analyzed in order to acquire a content of an operation performed by a user. Therefore, confidentiality of the inspection information is higher than that of an image.

Modified Example of First Embodiment

Figure 13:
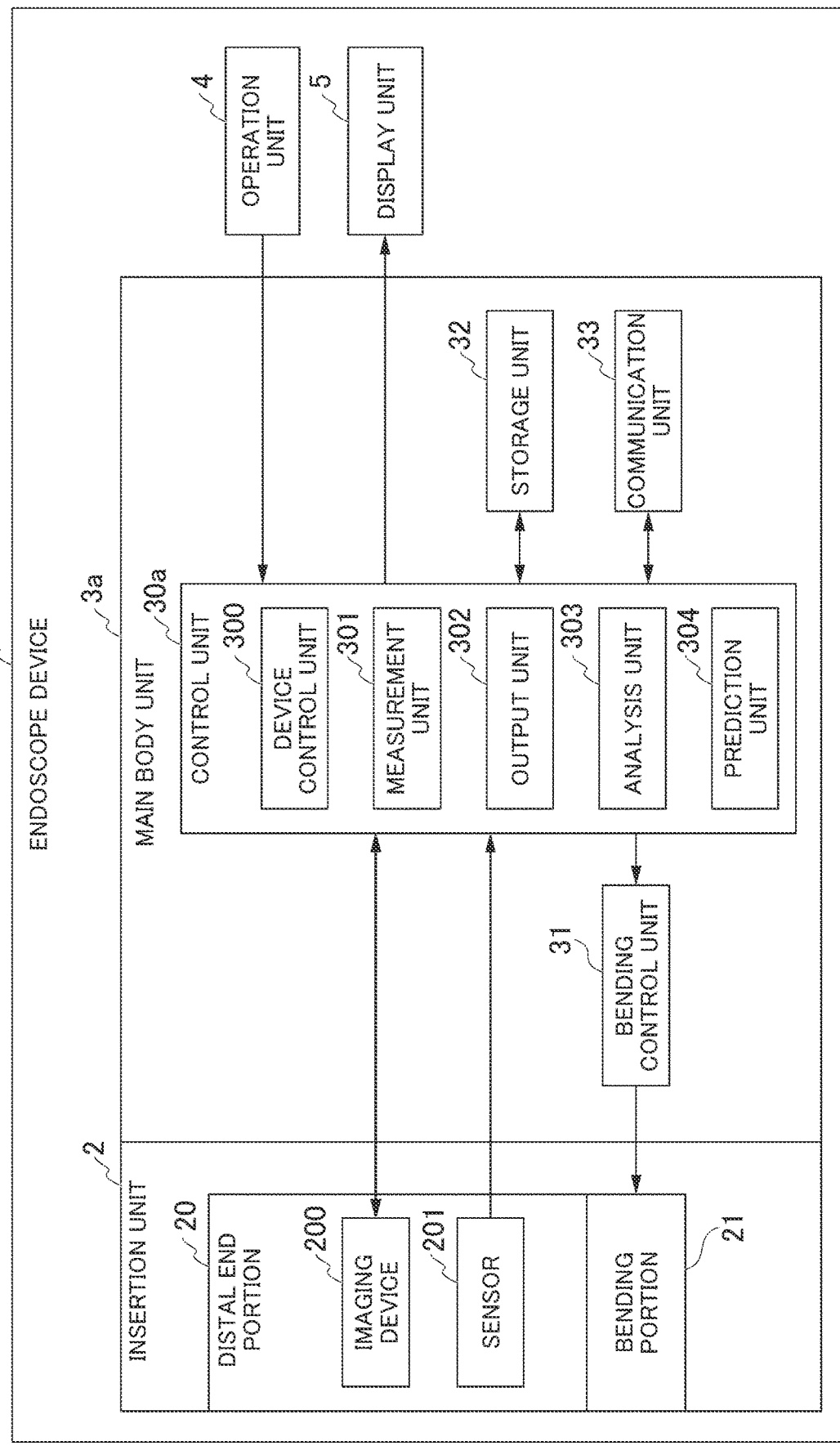
FIG. 13 is a block diagram showing a configuration of an endoscope device according to a modified example of the first embodiment of the present invention.

A modified example of the first embodiment of the present invention will be described. The endoscope device 1 shown in FIG. 3 is changed to an endoscope device 1*a* (inspection analysis device) shown in FIG. 13. FIG. 13 shows a configuration of the endoscope device 1*a*. The same configuration as that shown in FIG. 3 will not be described.

The main body unit 3 shown in FIG. 3 is changed to a main body unit 3*a* shown in FIG. 13. In the main body unit 3*a*, the control unit 30 shown in FIG. 3 is changed to a control unit 30*a* shown in FIG. 13. The control unit 30*a* includes a device control unit 300, a measurement unit 301, an output unit 302, an analysis unit 303, and a prediction unit 304.

The control unit 30*a* is constituted by at least one of a processor and a logic circuit. The control unit 30*a* may include one or a plurality of processors. The control unit 30*a* may include one or a plurality of logic circuits.

The analysis unit 303 has a similar function to that of the analysis unit 701 shown in FIG. 4. The analysis unit 303 analyzes inspection information stored on the storage unit 32 and generates operation data. The analysis unit 303 analyzes the inspection information of a past inspection and generates first operation data. In addition, the analysis unit 303 analyzes the inspection information of the latest inspection and generates second operation data.

The prediction unit 304 has a similar function to that of the prediction unit 702 shown in FIG. 4. The prediction unit 304 compares the first operation data and the second operation data with each other and predicts a state of an inspection target. The prediction unit 304 generates state information indicating the state of the inspection target.

The server 7 in the modified example of the first embodiment does not need to include the analysis unit 701 and the prediction unit 702 shown in FIG. 4.

Figure 14:
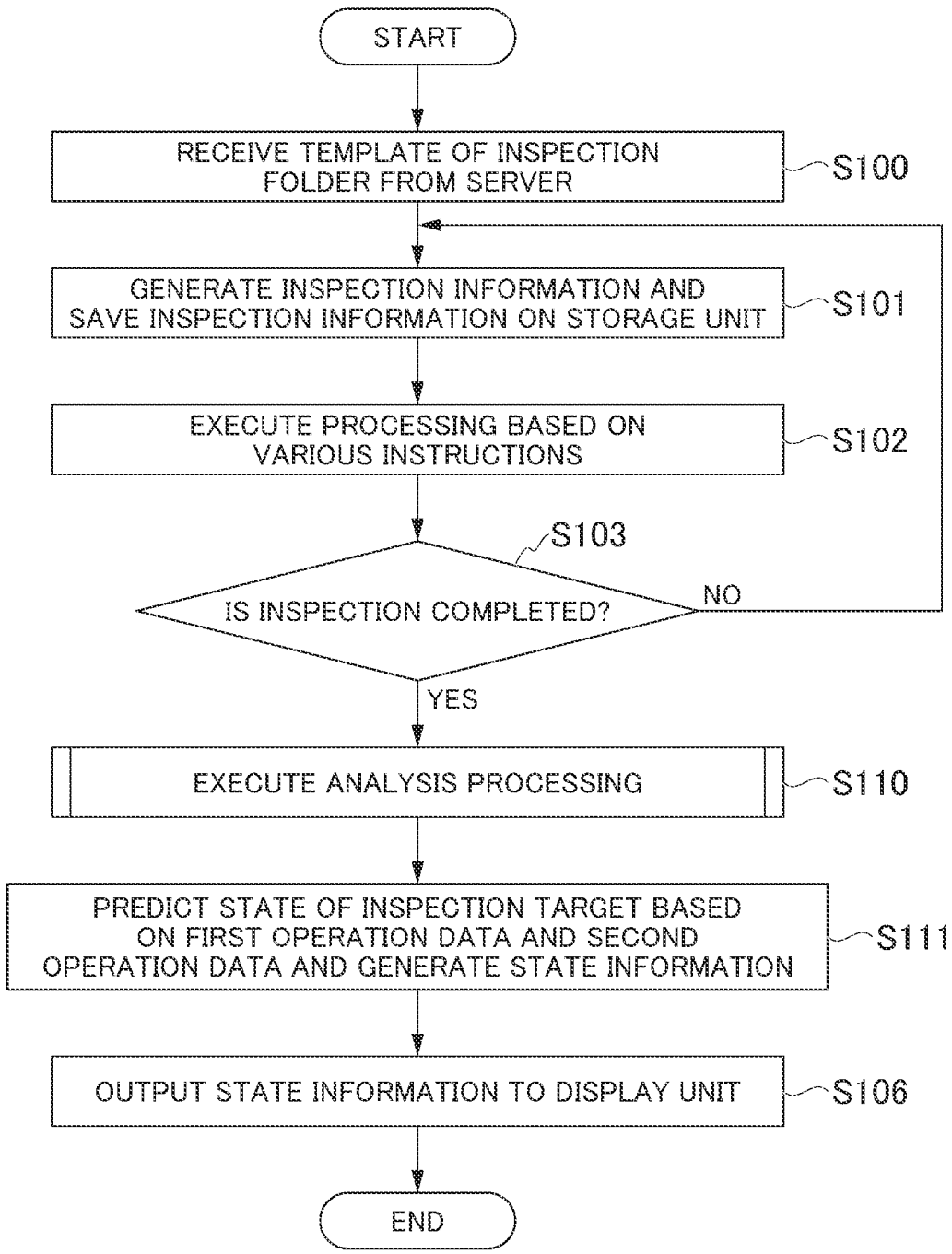
FIG. 14 is a flow chart showing a procedure of processing executed by the endoscope device according to the modified example of the first embodiment of the present invention.

Processing executed by the endoscope device 1*a* will be described by using FIG. 14. FIG. 14 shows a procedure of the processing executed by the endoscope device 1*a*. The same processing as that shown in FIG. 5 will not be described.

When the device control unit 300 determines that the inspection is completed in Step S103, the analysis unit 303 executes analysis processing (Step S110). The analysis processing in Step S110 is the same as that shown in FIG. 7.

After Step S110, the prediction unit 304 compares the first operation data and the second operation data with each other and predicts a state of an inspection target. The prediction unit 304 generates state information indicating the state of the inspection target (Step S111). The processing in Step S111 is the same as that in Step S203 shown in FIG. 6. After Step S111, Step S106 is executed.

The server 7 does not need to execute Steps S201 to S204 shown in FIG. 6. The storage unit 32 of the endoscope device 1*a* may store a template of an inspection folder in advance. Therefore, the server 7 does not need to execute Step S200 shown in FIG. 6.

An inspection analysis device according to each aspect of the present invention includes the analysis unit 303, the prediction unit 304, and the output unit 302. The analysis unit 303 analyzes inspection information related to an operation and generates operation data indicating a content of the operation. The prediction unit 304 compares first operation data and second operation data with each other and predicts a state of an inspection target. The first operation data indicate a content of an operation in a first inspection. The second operation data indicate a content of an operation in a second inspection performed after the first inspection is completed. The output unit 302 outputs state information indicating the state of the inspection target to the display unit 5 (reporting device).

In the modified example of the first embodiment, the analysis unit 303 analyzes the inspection information and generates operation data. The prediction unit 304 predicts a state of an inspection target on the basis of the operation data. Therefore, the endoscope device 1*a* can analyze an inspection result without requiring an image. A user can check a state of the inspection target.

Second Embodiment

A second embodiment of the present invention will be described. The inspection analysis system 10 provides a service of notifying a user of information related to skills of the user in an inspection.

Figure 15:
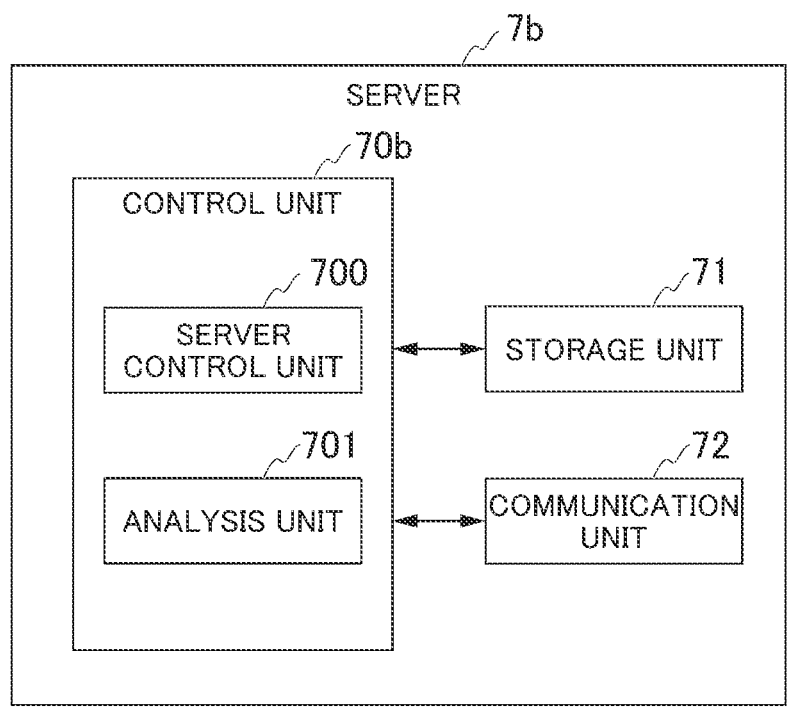
FIG. 15 is a block diagram showing a configuration of a server according to a second embodiment of the present invention.

The server 7 shown in FIG. 4 is changed to a server 7*b* (inspection analysis device) shown in FIG. 15. FIG. 15 shows a configuration of the server 7*b*. The same configuration as that shown in FIG. 4 will not be described.

The control unit 70 shown in FIG. 4 is changed to a control unit 70*b* shown in FIG. 15. The control unit 70*b* includes a server control unit 700 and an analysis unit 701.

The control unit 70b is constituted by at least one of a processor and a logic circuit. The control unit 70b may include one or a plurality of processors. The control unit 70b may include one or a plurality of logic circuits.

The analysis unit 701 analyzes the inspection information and generates operation data. The operation data indicate a content of an operation performed by a user in an inspection.

The operation data include at least one of a bending-times number, a bending amount, an insertion amount, and an insertion time. The bending-times number, the bending amount, the insertion amount, and the insertion time indicate a content of a first operation related to the insertion unit 2. The insertion time indicates the length of time during which the insertion unit 2 is inserted in an inspection target.

For example, the insertion time indicates the length of time from a timing at which the insertion unit 2 is inserted into the inspection target to a timing at which the insertion unit 2 reaches the deepest portion of the inspection target. Alternatively, the insertion time indicates the length of time during which the insertion unit 2 is pulled out from the deepest portion of the inspection target to the outside of the inspection target. The insertion time may be calculated on the basis of a temporal change in the insertion amount. A user may set the insertion time.

In addition, the operation data include at least one of a still-image-acquisition-times number, a measurement-execution-times number, a measurement result, a still image acquisition time, a measurement execution time, and a parameter-setting-times number. The still-image-acquisition-times number, the measurement-execution-times number, the measurement result, the still image acquisition time, the measurement execution time, and the parameter-setting-times number indicate a content of a second operation related to an image.

The still image acquisition time indicates the length of time required for acquiring a still image. For example, in a case in which two or more still images are acquired, the still image acquisition time indicates the length of time from a timing at which a still image is acquired first to a timing at which a still image is acquired last when the insertion amount is almost fixed.

The measurement execution time indicates the length of time required for executing the measurement. For example, in a case in which the measurement is executed twice or more, the measurement execution time indicates the length of time from a timing at which the measurement is executed first to a timing at which the measurement is executed last when the insertion amount is almost fixed.

The parameter-setting-times number indicates the number of times a parameter of image processing is set. The parameter of image processing indicates a parameter used for at least one of the brightness of an image, the strength of enhancement, and the strength of noise reduction.

The analysis unit 701 may calculate all of the still-image-acquisition-times number, the measurement-execution-times number, the measurement result, the still image acquisition time, the measurement execution time, and the parameter-setting-times number. The analysis unit 701 may calculate only some of the still-image-acquisition-times number, the measurement-execution-times number, the measurement result, the still image acquisition time, the measurement execution time, and the parameter-setting-times number.

The analysis unit 701 analyzes the inspection information of a past inspection and generates first operation data. In addition, the analysis unit 701 analyzes the inspection information of the latest inspection and generates second operation data. The communication unit 72 transmits the first operation data and the second operation data generated by the analysis unit 701 to the endoscope device 1.

The procedure of an inspection is determined in advance. In a case in which skills are uniform between users, the content of an operation is expected not to change between different inspections. However, there is a case in which skills are not uniform between users and the content of an operation changes between different inspections. The analysis unit 701 detects a change in an operation by analyzing the inspection information.

Differences from the first embodiment will be described regarding the configuration of the endoscope device 1. A user inputs a parameter-setting instruction into the endoscope device 1 by operating the operation unit 4. The parameter-setting instruction indicates an instruction to set a parameter of image processing. When the parameter-setting instruction is output from the operation unit 4, the device control unit 300 sets the parameter of the image processing. The device control unit 300 generates inspection information including the bending instruction, the still image acquisition instruction, the measurement instruction, the parameter-setting instruction, the sensor information, and time point information.

The communication unit 33 receives the first operation data and the second operation data transmitted from the server 7b. The output unit 302 outputs the first operation data and the second operation data to the display unit 5, thus displaying the first operation data and the second operation data on the display unit 5.

Figure 16:
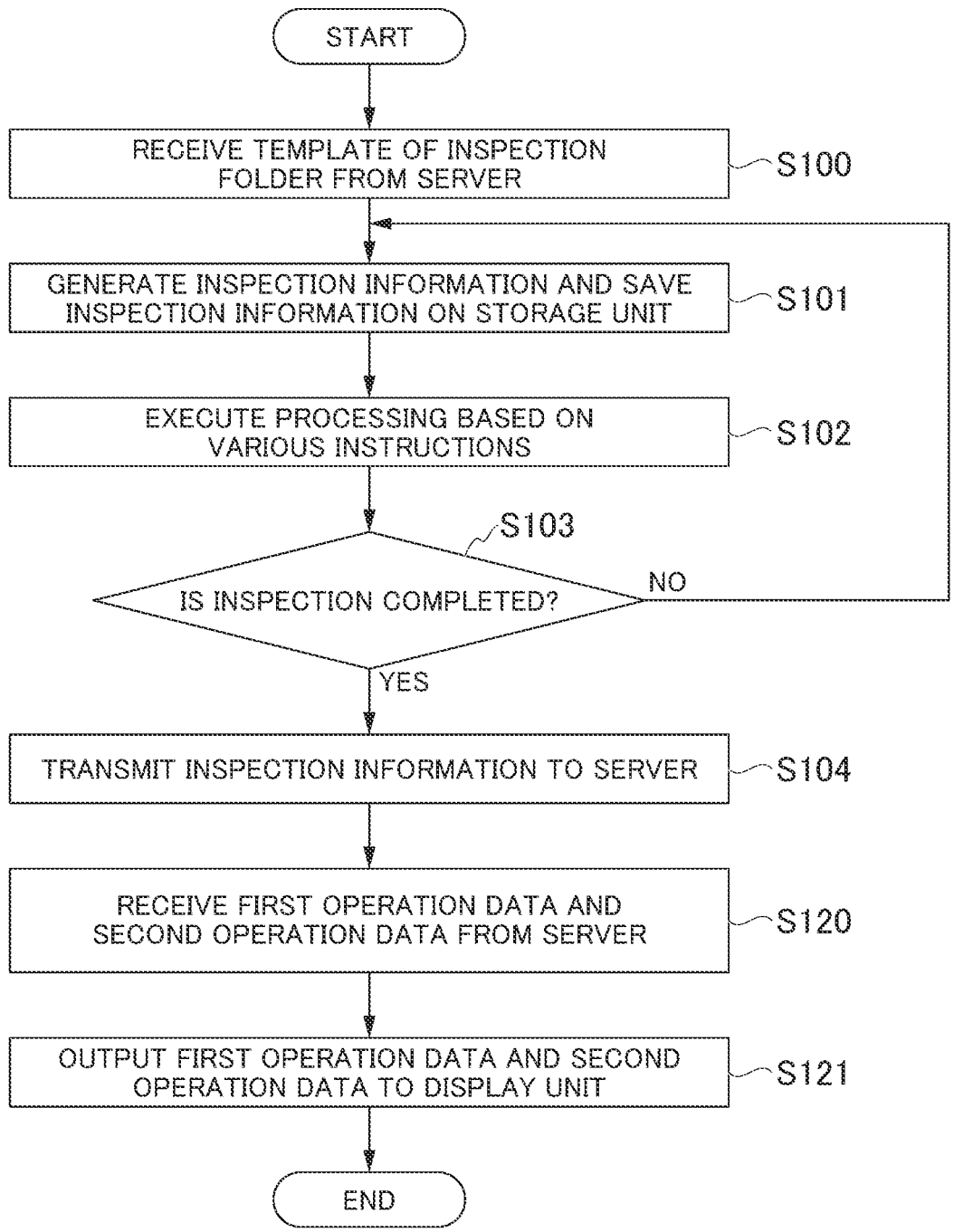
FIG. 16 is a flow chart showing a procedure of processing executed by an endoscope device according to the second embodiment of the present invention.

Processing executed by the endoscope device 1 will be described by using FIG. 16. FIG. 16 shows a procedure of the processing executed by the endoscope device 1. The same processing as that shown in FIG. 5 will not be described.

After Step S104, the device control unit 300 receives first operation data and second operation data transmitted from the server 7b by controlling the communication unit 33 (Step S120).

After Step S120, the output unit 302 outputs the first operation data and the second operation data received in Step S120 to the display unit 5 (Step S121). The display unit 5 displays the first operation data and the second operation data. For example, when an inspection is completed, Step S121 is executed. When Step S121 is executed, the processing shown in FIG. 16 is completed.

Figure 17:
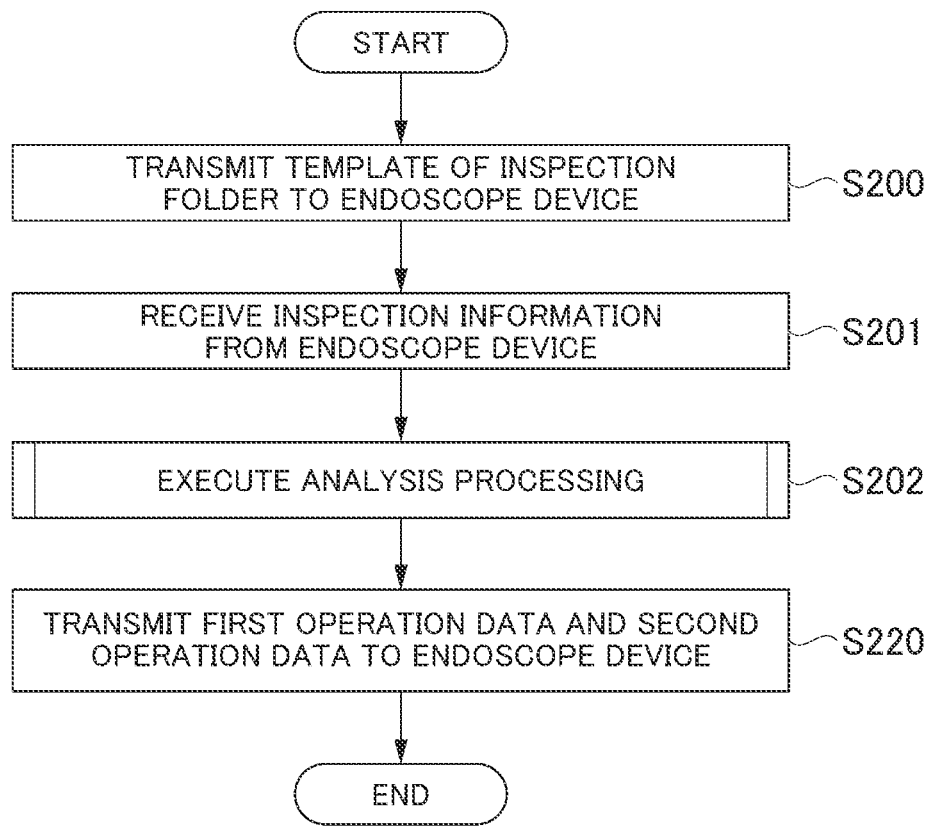
FIG. 17 is a flow chart showing a procedure of processing executed by the server according to the second embodiment of the present invention.

Processing executed by the server 7b will be described by using FIG. 17. FIG. 17 shows a procedure of the processing executed by the server 7b. The same processing as that shown in FIG. 6 will not be described.

After Step S202, the server control unit 700 transmits the first operation data and the second operation data generated in Step S202 to the endoscope device 1 by controlling the communication unit 72 (Step S220). When Step S220 is executed, the processing shown in FIG. 17 is completed.

Figure 18:
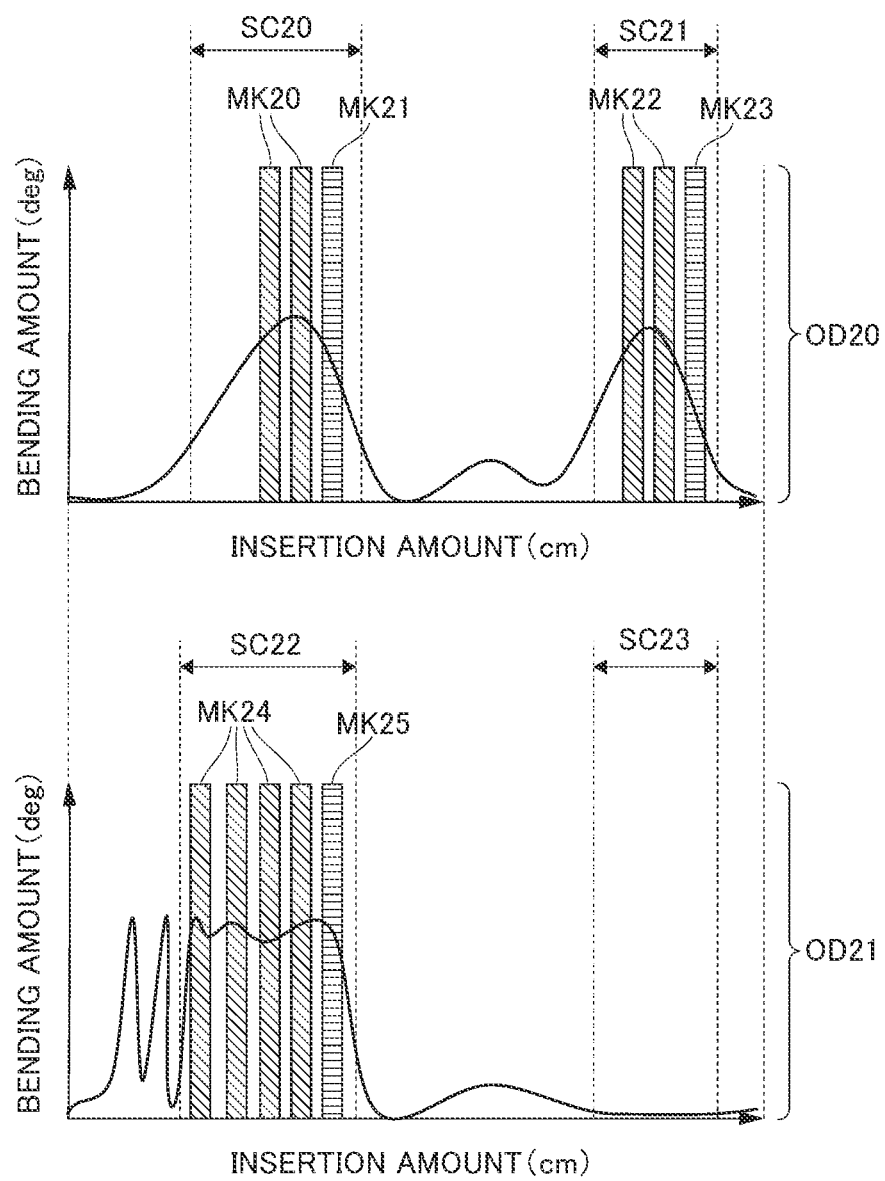
FIG. 18 is a diagram showing an example of operation data in the second embodiment of the present invention.

Operation data displayed on the display unit 5 will be described by using FIG. 18. FIG. 18 shows an example of the operation data displayed on the display unit 5. The endoscope device 1 assists a user's determination of his/her skills by displaying the operation data on the display unit 5.

First operation data OD20 indicate operation data in a past inspection. Second operation data OD21 indicate operation data in the latest inspection. The first operation data OD20 and the second operation data OD21 indicate a bending amount, a still-image-acquisition-times number, a measurement-execution-times number, and an insertion amount.

The relationship between the bending amount and the insertion amount is shown as a graph. The horizontal axis in the graph indicates the insertion amount, and the vertical axis in the graph indicates the bending amount. The insertion amount corresponds to a position in an inspection target. The analysis unit 701 associates the first operation data and the second operation data with each other on the basis of the insertion amount. The first operation data and the second operation data associated with each other are displayed on the display unit 5.

In the example shown in FIG. 18, the first operation data OD20 and the second operation data OD21 are arranged in the vertical direction. In a case in which a first insertion amount and a second insertion amount have the same value, the horizontal position of the first insertion amount at the value is the same as that of the second insertion amount at the value. The first insertion amount indicates an insertion amount in the first operation data OD20. The second insertion amount indicates an insertion amount in the second operation data OD21. A user can easily compare the first operation data OD20 and the second operation data OD21 with each other.

The bending amount is relatively large in a section SC20 and a section SC21 of the graph shown by the first operation data OD20. Marks MK20 and a mark MK21 are shown in the section SC20. Marks MK22 and a mark MK23 are shown in the section SC21.

The marks MK20 and the marks MK22 indicate positions at which a still image was acquired in the past inspection. The mark MK21 and the mark MK23 indicate positions at which the measurement was executed in the past inspection. In the section SC20, a still image was acquired twice as the marks MK20 show, and the measurement was executed once as the mark MK21 shows. In the section SC21, a still image was acquired twice as the marks MK22 show, and the measurement was executed once as the mark MK23 shows.

The bending amount is relatively large in a section SC22 of the graph shown by the second operation data OD21. Marks MK24 and a mark MK25 are shown in the section SC22.

The marks MK24 indicate positions at which a still image was acquired in the latest inspection. The mark MK25 indicates a position at which the measurement was executed in the latest inspection. In the section SC22, a still image was acquired four times as the marks MK24 show, and the measurement was executed once as the mark MK25 shows.

A user compares the first operation data OD20 and the second operation data OD21 with each other and determines his/her skills. When the past inspection was performed, a still image was acquired twice in the section SC20. When the latest inspection was performed, a still image was acquired four times in the section SC22 corresponding to the section SC20. The still-image-acquisition-times number in the latest inspection is greater than that in the past inspection. Therefore, the user may determine that his/her skills are poor. Fluctuations of the bending amount are great immediately before the section SC22. Therefore, it is presumable that positioning of a camera is unstable immediately before a still image is acquired. Fluctuations of the bending amount are seen also in the section SC22, and the user repeats acquiring a still image. Therefore, the user may determine that his/her skills are poor.

The user may determine his/her skills on the basis of the measurement-execution-times number. For example, in a case in which the measurement-execution-times number in the latest inspection is greater than that in the past inspection, it is presumed that the number of times the measurement fails is great. Therefore, the user may determine that his/her skills are poor.

When the past inspection was performed, a still image was acquired in the section SC21 and the measurement was executed. When the latest inspection was performed, a still image was not acquired in a section SC23 corresponding to the section SC21 and the measurement was not executed. Therefore, the user may determine that there is a possibility that an oversight of an inspection portion or an oversight of the damage occurred.

In many cases, a user checks the inspection portion with the bending portion 21 bending. When the past inspection was performed, the bending amount is relatively large in the section SC21. When the latest inspection was performed, the bending amount is small in the section SC23 corresponding to the section SC21. Therefore, the user may determine that there is a possibility that an oversight of an inspection portion or an oversight of the damage occurred.

The first operation data and the second operation data may indicate a bending-times number in the entire inspection. Alternatively, the first operation data and the second operation data may indicate a bending-times number when the insertion amount is almost fixed. The user may determine his/her skills on the basis of the bending-times number. There is a case in which the distal end portion 20 touches a structure in an inspection target and progress of the insertion unit 2 is hindered at the time of inserting the insertion unit 2. Therefore, a user inserts the insertion unit 2 into the inspection target while bending the bending portion 21. For example, in a case in which the bending-times number for the insertion amount in the latest inspection is greater than that for the insertion amount in the past inspection, the user may determine that his/her skills are poor.

The first operation data and the second operation data may indicate a bending-times number related to one bending direction. For example, in a case in which the bending-times number is greater than or equal to two, there is a possibility that a user repeatedly bended the bending portion 21 in the same direction. In this case, it is presumed that the user was unable to skillfully perform an operation for bending. Therefore, the user may determine that his/her skills are poor.

The first operation data and the second operation data may indicate a still image acquisition time or a measurement execution time. A user may determine his/her skills on the basis of the still image acquisition time or the measurement execution time. For example, in a case in which the still image acquisition time or the measurement execution time in the latest inspection is longer than that in the past inspection, the user cannot necessarily determine that his/her skills are poor. However, the user may determine that his/her skills are poor.

The first operation data and the second operation data may indicate a parameter-setting-times number. A user may determine his/her skills on the basis of the parameter-setting-times number. For example, in a case in which the parameter-setting-times number in the latest inspection is greater than that in the past inspection, it is presumed that the user failed in setting a parameter. Therefore, the user may determine that his/her skills are poor.

The first operation data and the second operation data may indicate a temporal change in an insertion amount. A user may determine his/her skills on the basis of the temporal change in the insertion amount. For example, if the length of time during which the insertion amount does not change is long, there is a possibility that it takes long to acquire a still image or execute the measurement. Therefore, the user may determine that his/her skills are poor. In a case in which the insertion amount repeatedly increases and decreases, it is presumed that the user often performs an unnecessary operation. Therefore, the user may determine that his/her skills are poor.

The analysis unit 701 may calculate an insertion time on the basis of the temporal change in the insertion amount. For example, when the insertion amount increases from zero, the analysis unit 701 determines that insertion is started. While the insertion amount continues to increase, the analysis unit 701 determines that the insertion continues. When the insertion amount stops increasing, the analysis unit 701 determines that the distal end portion 20 of the insertion unit 2 has reached a predetermined position. The analysis unit 701 may calculate an insertion time by calculating the length of time during which the insertion amount continues to increase. After the insertion unit 2 is inserted to the deepest portion of an inspection target, there is a case in which a user performs an inspection while pulling out the insertion unit 2. After the insertion unit 2 has reached the deepest portion of the inspection target, the analysis unit 701 may calculate an insertion time by calculating the length of time during which the insertion amount continues to decrease.

The analysis unit 701 may generate first operation data indicating the length of the insertion time in the past inspection. The analysis unit 701 may generate second operation data indicating the length of the insertion time in the latest inspection. A user may determine his/her skills on the basis of the length of the insertion time. For example, in a case in which the insertion time in the latest inspection is longer than that in the past inspection, the user may determine that his/her skills are poor.

The analysis unit 701 may generate a report including the first operation data and the second operation data. The endoscope device 1 may assist a user's determination of his/her skills by displaying the report on the display unit 5. FIG. 19 shows an example of the report.

A report RP20 shown in FIG. 19 includes first operation data OD22 and second operation data OD23. The report RP20 has a format of a table. The report RP20 indicates a value of each item in the first operation data OD22 and the second operation data OD23. In the report RP20, values of items of the first operation data OD22 in a past inspection and values of items of the second operation data OD23 in the latest inspection are arranged.

The output unit 302 may output only one of the first operation data and the second operation data to the display unit 5. For example, the communication unit 33 may receive only the second operation data from the server 7b in Step S120. The output unit 302 may output the second operation data to the display unit 5 in Step S121. A user may determine whether he/she performed an inspection in accordance with a predetermined procedure on the basis of only the second operation data.

The communication unit 33 may receive the first operation data and a template of an inspection folder from the server 7b in Step S100. The output unit 302 may output the first operation data to the display unit 5 prior to Step S101. A user may perform an inspection while referring to the first operation data. The value of each item of the first operation data does not need to be an average value in two or more past inspections and may be a value in an inspection performed once. For example, when a beginner undergoes training, he/she can refer to the first operation data in an inspection performed by an expert.

An inspection analysis method according to each aspect of the present invention provides a method of analyzing an operation performed by a user in an inspection performed by inserting the insertion unit 2 (endoscope) into an inspection target. The operation includes a first operation of the insertion unit 2 and a second operation related to an image generated by the imaging device 200 disposed in the distal end portion 20 of the insertion unit 2. The inspection analysis method includes an analysis step and an output step. The analysis unit 701 analyzes inspection information related to the operation and generates first operation data and second operation data indicating a content of the operation in the analysis step (Step S202). The first operation data indicate a content of an operation in a first inspection. The second operation data indicate a content of an operation in a second inspection performed after the first inspection is completed. The output unit 302 outputs the first operation data and the second operation data to the display unit 5 (reporting device) in the output step (Step S121).

An inspection analysis system according to each aspect of the present invention includes the server 7b (inspection analysis device) and the endoscope device 1. The server 7b includes the analysis unit 701 and the communication unit 72 (first communication unit). The analysis unit 701 analyzes inspection information related to an operation performed by a user and generates first operation data and second operation data indicating a content of the operation. The communication unit 72 receives the inspection information from the endoscope device 1 and transmits the first operation data and the second operation data to the endoscope device 1. The endoscope device 1 includes the insertion unit 2 (endoscope), the communication unit 33 (second communication unit), and the output unit 302. The communication unit 33 transmits the inspection information to the server 7b and receives the first operation data and the second operation data from the server 7b. The output unit 302 outputs the first operation data and the second operation data to the display unit 5 (reporting device).

Each aspect of the present invention may include the following modified example. The analysis unit 701 calculates, in the analysis step (Step S202), an insertion amount indicating the length of a portion of the insertion unit 2 (endoscope) inserted in the inspection target when the user performs an operation. The analysis unit 701 associates the first operation data and the second operation data with each other on the basis of an insertion amount in the analysis step.

Each aspect of the present invention may include the following modified example. The first operation data and the second operation data include at least one of a bending-times number of an endoscope, a bending amount of the endoscope, an insertion amount, and an insertion time. The insertion time indicates the length of time during which the insertion unit 2 is inserted in the inspection target. The insertion amount indicates the length of a portion of the insertion unit 2 inserted in the inspection target when the user performs an operation.

Each aspect of the present invention may include the following modified example. The endoscope is capable of being housed in a state of being wound around a reel. The insertion amount indicates the length of a portion of the endoscope pulled out of the reel.

Each aspect of the present invention may include the following modified example. The first operation data and the second operation data include at least one of the number of times a still image is acquired, the number of times measurement using an image is executed, the length of time required for acquiring the still image, the length of time required for executing the measurement, and the number of times a parameter of image processing using an image is set.

Each aspect of the present invention may include the following modified example. After a second inspection is completed, the output unit 302 outputs the first operation data and the second operation data to the display unit 5 (reporting device) in the output step (Step S121).

An inspection analysis method according to each aspect of the present invention provides a method of analyzing an operation performed by a user in an inspection performed by inserting the insertion unit 2 (endoscope) into an inspection target. The inspection analysis method includes an analysis step and an output step. The analysis unit 701 analyzes inspection information related to the operation and generates operation data indicating a content of the operation in the analysis step (Step S202). The output unit 302 outputs the operation data to the display unit 5 (reporting device) in the output step (Step S121).

In the second embodiment, the analysis unit 701 analyzes the inspection information and generates the operation data. The output unit 302 outputs the operation data to the display unit 5. Therefore, the inspection analysis system 10 can analyze an inspection result without requiring an image. A user can compare the content of an operation in a previously performed inspection and the content of an operation in the latest inspection with each other. The user can determine his/her skills on the basis of the comparison result.

Modified Example of Second Embodiment

Figure 20:
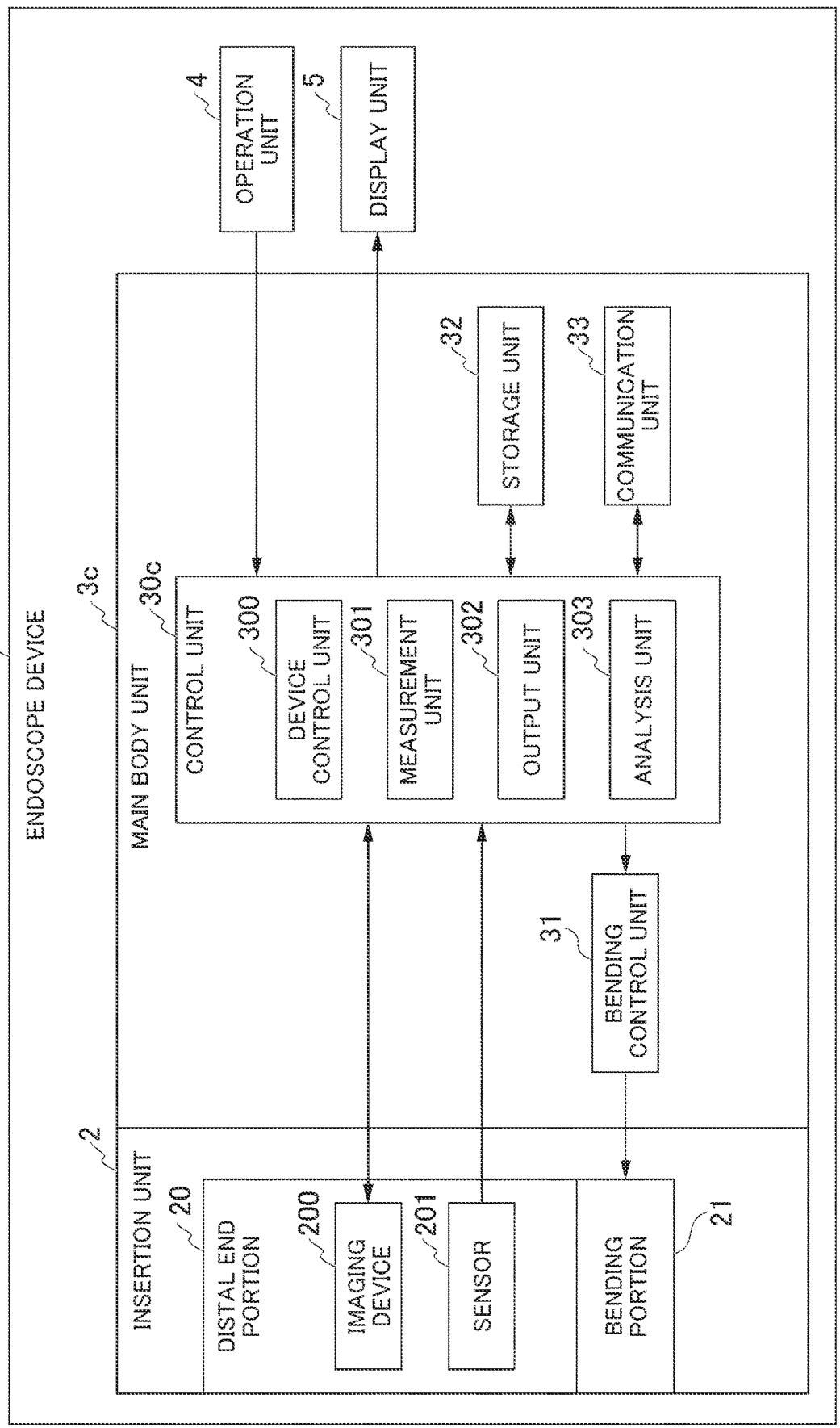
FIG. 20 is a block diagram showing a configuration of an endoscope device according to a modified example of the second embodiment of the present invention.

A modified example of the second embodiment of the present invention will be described. The endoscope device 1 shown in FIG. 3 is changed to an endoscope device 1c (inspection analysis device) shown in FIG. 20. FIG. 20 shows a configuration of the endoscope device 1c. The same configuration as that shown in FIG. 3 will not be described.

The main body unit 3 shown in FIG. 3 is changed to a main body unit 3c shown in FIG. 20. In the main body unit 3c, the control unit 30 shown in FIG. 3 is changed to a control unit 30c shown in FIG. 20. The control unit 30c includes a device control unit 300, a measurement unit 301, an output unit 302, and an analysis unit 303.

The control unit 30c is constituted by at least one of a processor and a logic circuit. The control unit 30c may include one or a plurality of processors. The control unit 30c may include one or a plurality of logic circuits.

The analysis unit 303 has a similar function to that of the analysis unit 701 shown in FIG. 4. The analysis unit 303 analyzes inspection information stored on the storage unit 32 and generates operation data. The analysis unit 303 analyzes the inspection information of a past inspection and generates first operation data. In addition, the analysis unit 303 analyzes the inspection information of the latest inspection and generates second operation data.

The server 7b in the modified example of the second embodiment does not need to include the analysis unit 701 shown in FIG. 15.

Processing executed by the endoscope device 1c will be described by using FIG. 21. FIG. 21 shows a procedure of the processing executed by the endoscope device 1c. The same processing as that shown in FIG. 16 will not be described.

When the device control unit 300 determines that the inspection is completed in Step S103, the analysis unit 303 executes analysis processing (Step S110). The analysis processing in Step S110 is the same as that shown in FIG. 7. After Step S110, Step S121 is executed.

The server 7b does not need to execute Step S201, Step S202, and Step S220 shown in FIG. 17. The storage unit 32 of the endoscope device 1c may store a template of an inspection folder in advance. Accordingly, the server 7b does not need to execute Step S200 shown in FIG. 17.

An inspection analysis device according to each aspect of the present invention includes the analysis unit 303 and the output unit 302. The analysis unit 303 analyzes inspection information related to an operation and generates first operation data and second operation data indicating a content of the operation. The first operation data indicate a content of an operation in a first inspection. The second operation data indicate a content of an operation in a second inspection performed after the first inspection is completed. The output unit 302 outputs the first operation data and the second operation data to the display unit 5 (reporting device).

In the modified example of the second embodiment, the analysis unit 303 analyzes the inspection information and generates the operation data. The output unit 302 outputs the operation data to the display unit 5. Therefore, the endoscope device 1c can analyze an inspection result without requiring an image. A user can compare the content of an operation in a previously performed inspection and the content of an operation in the latest inspection with each other. The user can determine his/her skills on the basis of the comparison result.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An inspection analysis method of analyzing an operation performed by a user in an inspection performed by inserting an endoscope into an inspection target, the inspection analysis method comprising:
   an analysis step in which a processor analyzes inspection information related to the operation and generates first operation data and second operation data indicating a content of the operation,
      wherein the operation includes a first operation of the endoscope and a second operation related to an image generated by an imaging device disposed in a distal end of the endoscope,
      wherein the first operation data indicate a content of the operation in a first inspection, and
      wherein the second operation data indicate a content of the operation in a second inspection performed after the first inspection is completed;
   a prediction step in which the processor compares the first operation data and the second operation data with each other and predicts a state of the inspection target; and
   an output step in which the processor outputs state information indicating the state to a reporting device,
      wherein the processor calculates, in the analysis step, an insertion amount indicating a length of a portion of the endoscope inserted in the inspection target when the user performs the operation,
      wherein the processor compares the first operation data and the second operation data with each other on the basis of the insertion amount in the prediction step,
      wherein the processor determines a start timing of the inspection and a completion timing of the inspection on the basis of the insertion amount in the analysis step, wherein the processor analyzes the inspection information generated from the start timing of the first inspection to the completion timing of the first inspection and generates the first operation data in the analysis step, and wherein the processor analyzes the inspection information generated from the start timing of the second inspection to the completion timing of the second inspection and generates the second operation data in the analysis step.

2. The inspection analysis method according to claim 1, wherein the first operation data and the second operation data include at least one of a bending-times number of the endoscope, a bending amount of the endoscope, and an insertion amount, wherein the bending-times number indicates the number of times the endoscope bends, wherein the bending amount indicates an amount of a change in an angle of the distal end when the endoscope bends, and wherein the insertion amount indicates a length of a portion of the endoscope inserted in the inspection target when the user performs the operation.

3. The inspection analysis method according to claim 2, wherein the endoscope is capable of being housed in a state of being wound around a reel, and wherein the insertion amount indicates a length of a portion of the endoscope pulled out of the reel.

4. The inspection analysis method according to claim 1, wherein the endoscope is capable of being housed in a state of being wound around a reel, and wherein the insertion amount indicates a length of a portion of the endoscope pulled out of the reel.

5. The inspection analysis method according to claim 1, wherein the first operation data and the second operation data include at least one of the number of times a still image is acquired, the number of times measurement using the image is executed, and a result of the measurement.

6. The inspection analysis method according to claim 1, wherein a type of the inspection target in the second inspection is the same as that of the inspection target in the first inspection, and wherein an individual of the inspection target in the second inspection is the same as or different from that of the inspection target in the first inspection.

7. The inspection analysis method according to claim 1, wherein, after the second inspection is completed, the processor outputs the state information to the reporting device in the output step.

8. An inspection analysis method of analyzing an operation performed by a user in an inspection performed by inserting an endoscope into an inspection target, the inspection analysis method comprising:

an analysis step in which a processor analyzes inspection information related to the operation and generates first operation data and second operation data indicating a content of the operation,
wherein the operation includes a first operation of the endoscope and a second operation related to an image generated by an imaging device disposed in a distal end of the endoscope,
wherein the first operation data indicate a content of the operation in a first inspection, and
wherein the second operation data indicate a content of the operation in a second inspection performed after the first inspection is completed; and an output step in which the processor outputs the first operation data and the second operation data to a reporting device, wherein the processor calculates, in the analysis step, an insertion amount indicating a length of a portion of the endoscope inserted in the inspection target when the user performs the operation, wherein the processor associates the first operation data and the second operation data with each other on the basis of the insertion amount in the analysis step, wherein the processor determines a start timing of the inspection and a completion timing of the inspection on the basis of the insertion amount in the analysis step, wherein the processor analyzes the inspection information generated from the start timing of the first inspection to the completion timing of the first inspection and generates the first operation data in the analysis step, and wherein the processor analyzes the inspection information generated from the start timing of the second inspection to the completion timing of the second inspection and generates the second operation data in the analysis step.

9. The inspection analysis method according to claim 8, wherein the first operation data and the second operation data include at least one of a bending-times number of the endoscope, a bending amount of the endoscope, an insertion amount, and an insertion time, wherein the bending-times number indicates the number of times the endoscope bends, wherein the bending amount indicates an amount of a change in an angle of the distal end when the endoscope bends, wherein the insertion amount indicates a length of a portion of the endoscope inserted in the inspection target when the user performs the operation, and wherein the insertion time indicates a length of time during which the endoscope is inserted in the inspection target.

10. The inspection analysis method according to claim 9, wherein the endoscope is capable of being housed in a state of being wound around a reel, and wherein the insertion amount indicates a length of a portion of the endoscope pulled out of the reel.

11. The inspection analysis method according to claim 8, wherein the endoscope is capable of being housed in a state of being wound around a reel, and wherein the insertion amount indicates a length of a portion of the endoscope pulled out of the reel.

12. The inspection analysis method according to claim 8, wherein the first operation data and the second operation data include at least one of the number of times a still image is acquired, the number of times measurement using the image is executed, a length of time required for acquiring the still image, a length of time required for executing the measurement, and the number of times a parameter of image processing using the image is set.

13. The inspection analysis method according to claim 8, wherein a type of the inspection target in the second inspection is the same as that of the inspection target in the first inspection, and wherein an individual of the inspection target in the second inspection is the same as or different from that of the inspection target in the first inspection.

14. The inspection analysis method according to claim 8, wherein, after the second inspection is completed, the processor outputs the first operation data and the second operation data to the reporting device in the output step.

15. An inspection analysis system that analyzes an operation performed by a user in an inspection performed by inserting an endoscope into an inspection target, the inspection analysis system comprising:
- an inspection analysis device comprising:
  - a first processor configured to:
    - analyze inspection information related to the operation,
      - wherein the operation includes a first operation of the endoscope and a second operation related to an image generated by an imaging device disposed in a distal end of the endoscope;
    - generate first operation data and second operation data indicating a content of the operation,
      - wherein the first operation data indicate a content of the operation in a first inspection, and
      - wherein the second operation data indicate a content of the operation in a second inspection performed after the first inspection is completed;
    - compare the first operation data and the second operation data with each other; and
    - predict a state of the inspection target; and
  - a first communicator configured to receive the inspection information from an endoscope device and transmit state information indicating the state to the endoscope device; and
- the endoscope device comprising:
  - the endoscope;
  - a second communicator configured to transmit the inspection information to the inspection analysis device and receive the state information from the inspection analysis device; and
  - a second processor configured to output the state information to a reporting device,
- wherein the first processor calculates an insertion amount indicating a length of a portion of the endoscope inserted in the inspection target when the user performs the operation,
- wherein the first processor compares the first operation data and the second operation data with each other on the basis of the insertion amount,
- wherein the first processor determines a start timing of the inspection and a completion timing of the inspection on the basis of the insertion amount,
- wherein the first processor analyzes the inspection information generated from the start timing of the first inspection to the completion timing of the first inspection and generates the first operation data, and
- wherein the first processor analyzes the inspection information generated from the start timing of the second inspection to the completion timing of the second inspection and generates the second operation data.

16. An inspection analysis system that analyzes an operation performed by a user in an inspection performed by inserting an endoscope into an inspection target, the inspection analysis system comprising:
- an inspection analysis device comprising:
  - a first processor configured to:
    - analyze inspection information related to the operation,
      - wherein the operation includes a first operation of the endoscope and a second operation related to an image generated by an imaging device disposed in a distal end of the endoscope; and
    - generate first operation data and second operation data indicating a content of the operation,
      - wherein the first operation data indicate a content of the operation in a first inspection, and
      - wherein the second operation data indicate a content of the operation in a second inspection performed after the first inspection is completed; and
  - a first communicator configured to receive the inspection information from an endoscope device and transmit the first operation data and the second operation data to the endoscope device; and
- the endoscope device comprising:
  - the endoscope;
  - a second communicator configured to transmit the inspection information to the inspection analysis device and receive the first operation data and the second operation data from the inspection analysis device; and
  - a second processor configured to output the first operation data and the second operation data to a reporting device,
- wherein the first processor calculates an insertion amount indicating a length of a portion of the endoscope inserted in the inspection target when the user performs the operation,
- wherein the first processor associates the first operation data and the second operation data with each other on the basis of the insertion amount,
- wherein the first processor determines a start timing of the inspection and a completion timing of the inspection on the basis of the insertion amount,
- wherein the first processor analyzes the inspection information generated from the start timing of the first inspection to the completion timing of the first inspection and generates the first operation data, and
- wherein the first processor analyzes the inspection information generated from the start timing of the second inspection to the completion timing of the second inspection and generates the second operation data.

* * * * *